(12) United States Patent
Seeman et al.

(10) Patent No.: US 6,255,469 B1
(45) Date of Patent: Jul. 3, 2001

(54) PERIODIC TWO AND THREE DIMENSIONAL NUCLEIC ACID STRUCTURES

(75) Inventors: Nadrian Seeman, New York, NY (US); Erik Winfree, Princeton, NJ (US); Furong Liu, New York, NY (US); Lisa Wenzler Savin, Indianapolis, IN (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/306,405

(22) Filed: May 6, 1999

Related U.S. Application Data

(60) Provisional application No. 60/084,402, filed on May 6, 1998.

(51) Int. Cl.[7] .................................................. C07H 21/00
(52) U.S. Cl. ........................................ 536/23.1; 536/25.3
(58) Field of Search ................................. 536/23.1, 24.1, 536/24.2, 24.5, 25.3

(56) References Cited

U.S. PATENT DOCUMENTS 6,072,044 * 6/2000 Seeman et al. ..................... 536/22.1

OTHER PUBLICATIONS

Winfree et al., "On the Computational Power of DNA Annealing and Ligation", *DIAMACS Series in Discrete Mathematics and Theoretical Computers Science*, vol. 27, pp. 199–221, (1995).

Li et al., "Antiparallel DNA Double Crossover Molecules As Components for Nanoconstruction", *Journal of the American Chemical Society*, vol. 118, No. 26, pp. 6131–6140, (1996).

* cited by examiner

*Primary Examiner*—John S. Brusca
(74) *Attorney, Agent, or Firm*—Browdy & Neimark

(57) ABSTRACT

Two- and three-dimensional periodic lattices are constructed from repeating units of at least two antiparallel nucleic acid multi-crossover molecules. The repeating units range from single component to multi-component.

17 Claims, 21 Drawing Sheets

DAE

DAO

DX+2J

DAO-E

DAO-O

DAE-O

DAE-E

DAE-DAO

FIG. 9A

```
strand 1
ACTATGCTAGTCC  TGTATGTCATGCCGTTGTGCC  TGAGCACCAGTCG
        GATCAGG  ACATACAGTACGGCAACACGG  ACTCGTGGTCAGCCGTCAG
strand 2               strand 3                    strand 4

CACAGCGGTAGCGT  CCGATACGATGCAGTACGTGT  CCGTAGTTGCTGG
        CCATCGCA  GGCTATGCTACGTCATGCACA  GGCATCAACGACCGCAGTC
                                                    strand 5
```

FIG. 9B

```
   T
  T  ATGCCAGCTG  TA   T
  T  TACGGTCGAC  AT   T
   T strand 1
GCAGTCGCACGACC  TGGCGT   TGTACTACGCAATCC  TGCCGTATCGACG
        CGTGCTGG  ACCGCA   ACATGATGCGTTAGG  ACGGCATAGCTGCCTACCG
strand 2                strand 3                    strand 4

CGTCAGGCTGCTGT  CCGATGCGGT  CACTGGTTAGT   CCATGATGCACG
        CGACGACA  GGCTACGCCA  GTGACCAATCA   GGTACTACGTGCCATCGC
                                                    strand 5
                                  T
                      T CTCAGCTG  CCTA  T
                      T GAGTCGAC  GGAT  T
                                        T
```

FIG. 9C

```
                        strand 3
    T                                    T
   T  GAGCC        GACACCACGAG   T
   T  CTCGGCTGTGG         TGCTC   T
    T              Strand 2
strand 1
GCAGTCGCACGACC  TGGCGT   TGTACTACGCAATCC  TGCCGTATCGACG
        CGTGCTGG  ACCGCA   ACATGATGCGTTAGG  ACGGCATAGCTGCCTACCG
strand 4                strand 5                    strand 6

CGTCAGGCTGCTGT  CCGATGCGGT  CACTGGTTAGT   CCATGATGCACG
        CGACGACA  GGCTACGCCA  GTGACCAATCA   GGTACTACGTGCCATCGC
                                                    strand 7
                                          strand 8      T
                    T  GCAAC      GCTTCGCTGAC       T
                    T  CGTTGCGAAGC       GACTG      T
                                                    T
                        strand 9
```

FIG. 9D

```
                                    strand 1
         ─────────────────────────────────────────────────────────▶
         GATGGCGACATCC  TGCCGCTATGATTACACAGCC  TGAGCATTGACAC
                CTGTAGG  ACGGCGATACTAATGTGTCGG  ACTCGTAACTGTGACTTGA
strand 2              ◀───┐┌─                 ─┐┌─                 ─
◀─────────────            │└─     strand 3    ─┘│      strand 4    
         GTAGCGCCGTTAGT  CCAACTGGCATGTAGTATCGT  CCGATTCAACCAG
              GGCAATCA  GGTTGACCGTACATCATAGCA  GGCTAAGTTGGTCGTTGCT
                                                              strand 5
         ◀─────────────────────────────────────────────────────────
```

FIG. 9E

```
              T
           T    AGCATGTTGCCAGC   T
           T    TCGTACAACGGTCG   T
              T                T
strand 1
         ─────────┐         ┌─────────────────────────────────────▶
         TGAACTCGGCAGCC  TGTAAC    GGTTGGTCGCTATCC  TGATGACACTACG
                 GCCGTCGG  ACATTG  CCAACCAGCGATAGG  ACTACTGTGATGCTGATAC
strand 2        ◀─┐┌─              ─┐┌─                  ─
◀─────────────    │└─  strand 3    ─┘│      strand 4     
         CAACGAGCAATCGT  CCGATGCGGT  ACATACGCAGT  CCAGTTGTATCG
              CGTTAGCA  GGCTACGCCA  TGTATGCGTCA  GGTCAACATAGCGTGTCG
                                                           strand 5
         ◀────────────────────────────────┘         └──────
                                           T  GTGACGTGCTGACA    T
                                           T  CACTGCACGACTGT    T
                                                              T
```

FIG. 13A
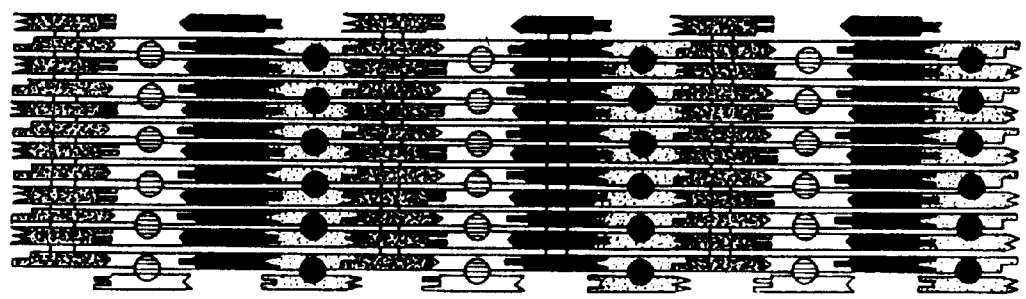
↓ RESTRICT   ↓ RESTRICT   ↓ RESTRICT
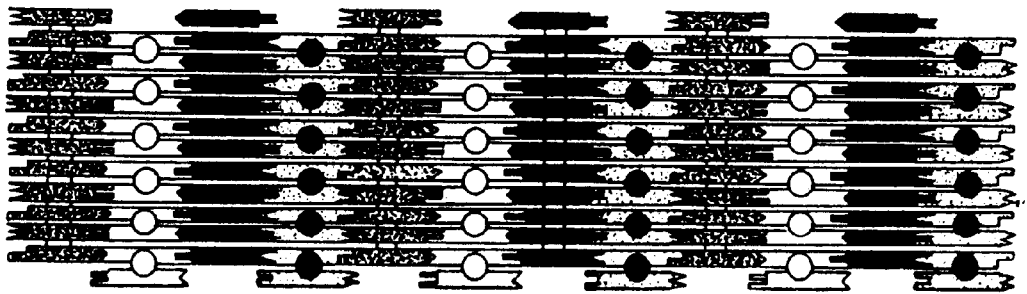
FIG. 13B

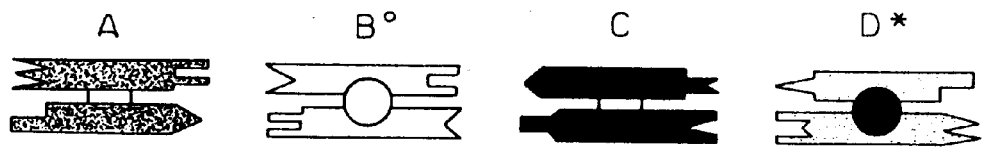
FIG. 13C
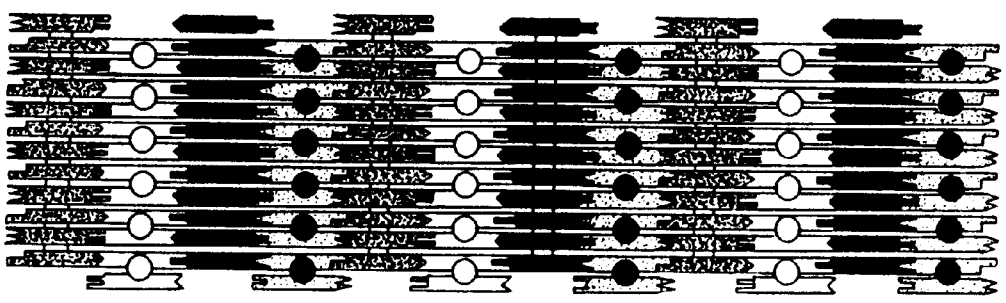
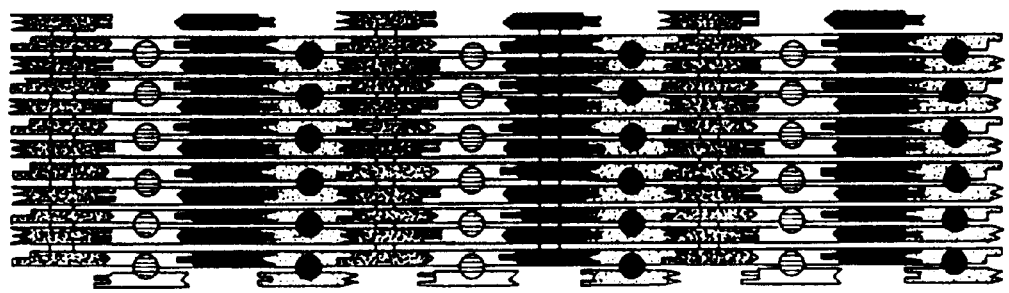
FIG. 13D

PERIODIC TWO AND THREE DIMENSIONAL NUCLEIC ACID STRUCTURES

CROSS-REFERENCE TO RELATED APPLICATION

The present application claims priority under 35 U.S.C. §119(e) from U.S. provisional application No. 60/084,402, filed May 6, 1998, the entire content of which is hereby incorporated by reference.

GOVERNMENT LICENSE RIGHTS

The experiments performed in this application were supported in part by the Office of Naval Research, grant no. N00014-98-1-0093; the National Institute of General Medical Sciences, grant no. R01GM-29554-16; the National Science Foundation and Defense Advanced Research Projects Agency, grant no. NSF-CCR-97-25021; the National Institute of Mental Health Training, grant no. 5 T32 MH 19138-07; and the National Science Foundation Engineering Research Center Program, grant no. EEC-9402726. The U.S. Government has a paid up license in this invention and the right in limited circumstances to require the patent owner to license others on reasonable terms as provided by the terms of the above grants.

BACKGROUND OF THE INVENTION

1. Field of the Invention

The present invention relates to two-dimensional and three-dimensional polynucleic acid nanostructures which are periodic and thereby translationally symmetrical.

2. Description of The Related Art

A key aim of biotechnology and nanotechnology (Feynman et al, 1961, and Drexler, 1981) is a rational approach to the construction of new biomaterials, including individual geometrical objects and nanomechanical devices, and extended constructions, particularly periodic matter with control of the molecule architecture such that it would permit the fabrication of intricate arrangements of atoms to serve many practical purposes (Robinson et al, 1987; Seeman, 1991a; Seeman, 1991b). The informational macromolecules of biological systems, proteins and nucleic acids, are believed to have the potential to serve as building blocks for these constructions, because they are used for similar purposes in the cell. For instance, nanometer-scale circuitry and robotics could accomplish many tasks that are impossible today. One can envision improvements in the storage and retrieval of information, directed attacks on the molecular basis of medical problems, and the assembly of very smart materials as possible end products of the ability to control the structure of matter on the nanometer scale.

There are at least three key elements necessary for the control of three-dimensional structure in molecular construction that involves the high symmetry associated with crystals: (1) the predictable specificity of intermolecular interactions between components; (2) the structural predictability of intermolecular products; and (3) the structural rigidity of the components (Liu et al, 1994). DNA branched junctions are excellent building blocks from the standpoint of the first two requirements, which are also needed for the construction of individual objects, because (1) ligation directed by Watson-Crick base pairing between sticky-ended molecules has been used successfully to direct intermolecular specificity since the early 1970's (Cohen et al, 1973); and (2) the ligated product is double helical B-DNA, whose local structural parameters are well-known (Arnott et al, 1973).

The key problem in working with branched DNA as a construction medium is that branched junctions have been shown to be extremely flexible molecules (Ma et al, 1986; Petrillo et al, 1988). The ligation of 3-arm and 4-arm DNA branched junctions leads to many different cyclic products, suggesting that the angles between the arms of the junctions vary on the ligation time-scale; these angles are analogous to valence angles around individual atoms. Likewise, a 5-arm DNA branched junction has been shown to have no well-defined structure, and a 6-arm DNA branched junction has only a single preferred stacking domain (Wang et al, Biochem. 30:5667–5674). Leontis and his colleagues have shown that a three-arm branched junction containing a loop of two deoxythymidine nucleotides has a preferred stacking direction (Leontis et al, 1991) and ligation along this direction shows a lower propensity to cyclization (21.3%) than other directions (Liu et al, 1994), but it is not possible to treat the stacking domain in the Leontisian junction as a rigid component (Qi et al, 1996).

To overcome the problem of branched DNA being extremely flexible and therefore unsuitable from the standpoint of structural rigidity of the components as the third key element, DNA structures that fail to cyclize significantly in the course of ligation reactions (a measure of the rigidity of the DNA) were sought by the present inventors. DNA double crossover molecules, which are model systems for structures proposed to be involved in genetic recombination initiated by double strand breaks (Sun et al, 1991; Thaler et al, 22:169–197, 1988), as well as meiotic recombination (Schwacha et al, 1995), were explored with respect to the structural features of these molecules, and a laboratory of the inventors has shown that there are five different isomers of double crossover molecules (Fu et al, 1993). Double crossover molecules were used in the laboratory of the present inventor to establish the sign of the crossover node in the Holliday junction (Fu et al, 1994b), to construct symmetric immobile branched junctions (Zhang et al, 1994b), and to examine the effect of domain orientation on cleavage by the Holliday junction resolvase, endonuclease VII (Fu et al, 1994a). The helical domains were found to be parallel in three of the five isomers, and antiparallel in the other two. Those with parallel domains are not as well-behaved as those with antiparallel domains (Fu et al, 1993).

A laboratory of the present inventors reported the design of geometrical objects and lattices composed of rigid motifs, such as triangles and deltahedra, etc., formed from antiparallel nucleic acid double crossover molecules (Li et al, 1996; WO 97/41142). These findings stimulated a theoretical proposal to use aperiodic two-dimensional (2-D) lattices of double crossover molecules (Winfree, 1996) for DNA-based computation (Adleman, 1994). In the mathematical theory of tiling (Grunbaum et al, 1986), rectangular tiles with programmable interactions, known as Wang tiles, can be designed so that their assembly must mimic the operation of a chosen Turing Machine (H. Wang, 1963). Double crossover molecules acting as molecular Wang tiles could self-assemble to perform desired computations (Winfree, 1996).

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a two-dimensional periodic lattice formed of coplanar repeating units, each of which is composed of at least two antiparallel nucleic acid multi-crossover molecules. Anti-parallel nucleic acid multi-crossover molecules are connected to an adjacent antiparallel nucleic acid multi-crossover molecule either within a repeating unit or between adjacent repeating units by complementary cohesive ends. The at least two antiparallel nucleic acid crossover molecules in a repeating unit are either the same antiparallel nucleic acid multi-crossover molecule or a multi-component arrangement of different antiparallel nucleic acid multi-crossover molecules.

The present invention also provides for a three-dimensional periodic lattice which may be formed as an extension of the two-dimensional period lattice into a third dimension, such as by interconnecting adjacent two-dimensional lattices by joining together antiparallel nucleic acid multi-crossover molecules in adjacent planes. The present invention provides antiparallel nucleic acid crossover molecules with a helical arm or domain which projects out of the plane of a two-dimensional lattice to connect by complementary cohesive ends to a corresponding helical arm from an adjacent two-dimensional lattice and produce a stacking of two-dimensional lattices.

BRIEF DESCRIPTION OF THE DRAWINGS

FIGS. 2C and 2D show the lattice topologies produced by the DAO (FIG. 2C) and DAE (FIG. 2D) units with specific spacings. Arrowheads indicate the 3' ends of strands. Black ellipses indicate dyad symmetry axes perpendicular to the plane; black arrows indicate dyad axes in the plane (full arrowhead) or screw axes (half arrowhead). The symmetries of the DAO-E and DAE-O lattices are those corresponding to the layer groups (Vainshtein, 1994) $p2_122$ and $p2_12_12$ respectively. The boundaries of the DAE-O units are not designed to coincide with the vertical symmetry elements.

In FIGS. 5A and 5B, model structures for DAO and DAE type A units, respectively, are shown. The crossover points are circled. Complete base stacking at the crossover points is assumed. Computer models showing every nucleotide (nt) were generated using NAMOT2 (Carter et al, 1996). The schematics accurately report intended primary and secondary structure—oligonucleotide sequence and paired bases—but are not geometrically or topologically faithful because they do not show the double helical twist. Both DAO-E and DAE-O type A (FIGS. 5C and 5D, respectively), type B (FIGS. 5E and 5F, respectively) and type B' (FIGS. 5G and 5H, respectively) are shown, indicating where the hairpin sequences are inserted. The sequences shown in FIGS. 5C–5H are as follows:

Figure 5B:
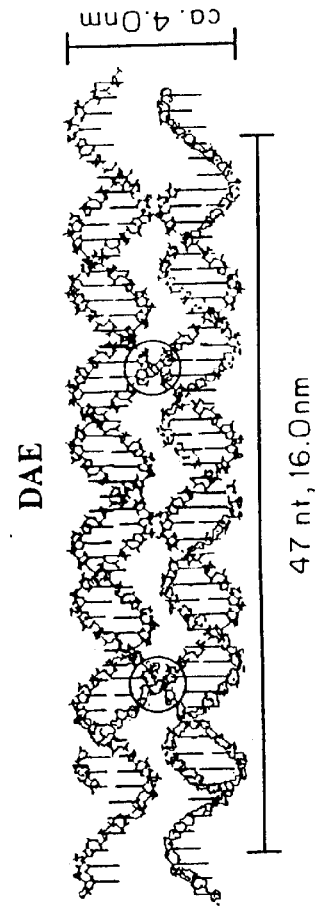
FIGS. 5A–5H show the molecular structure and design of DAO and DAE molecules.
Figure 5A:
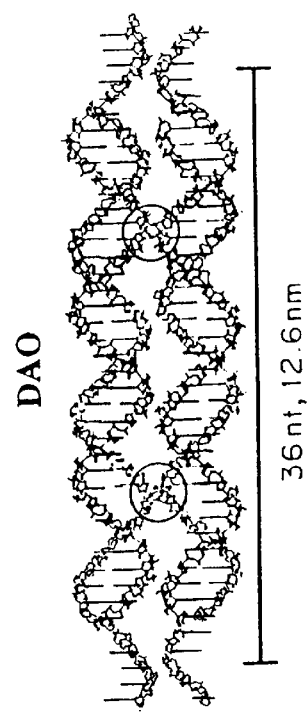
Figure 5C:
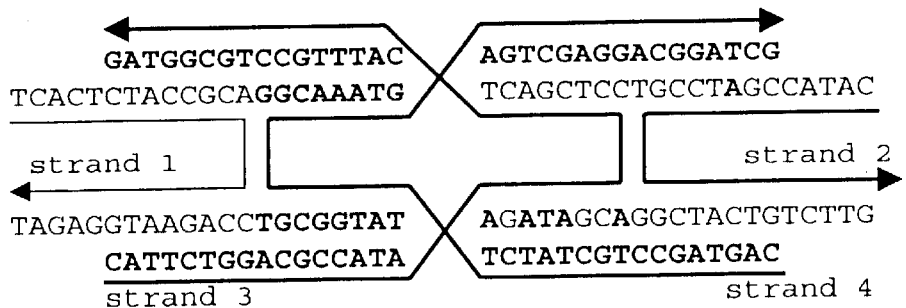
Figure 5D:
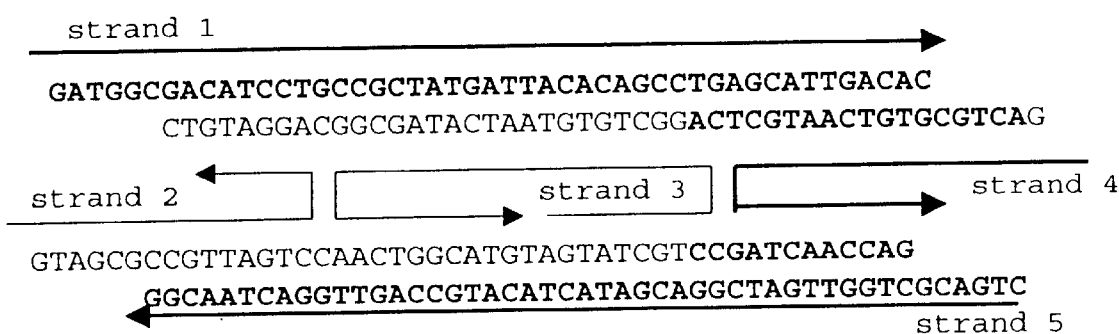
Figure 5E:
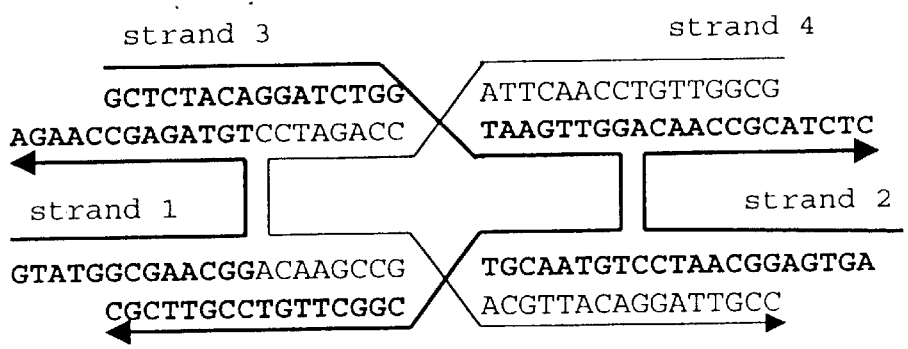
Figure 5F:
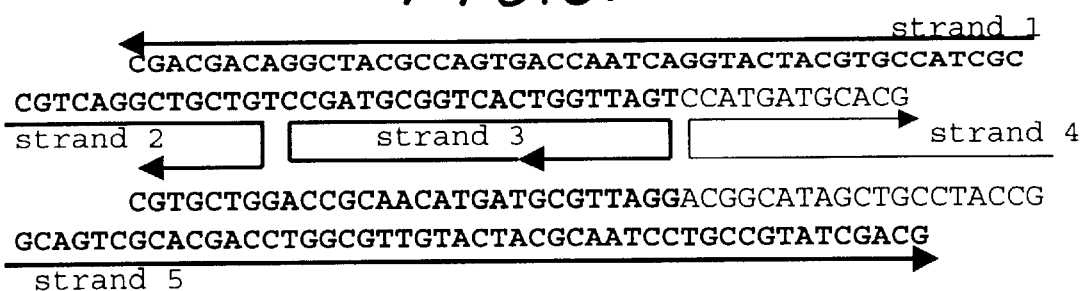
Figure 5G:
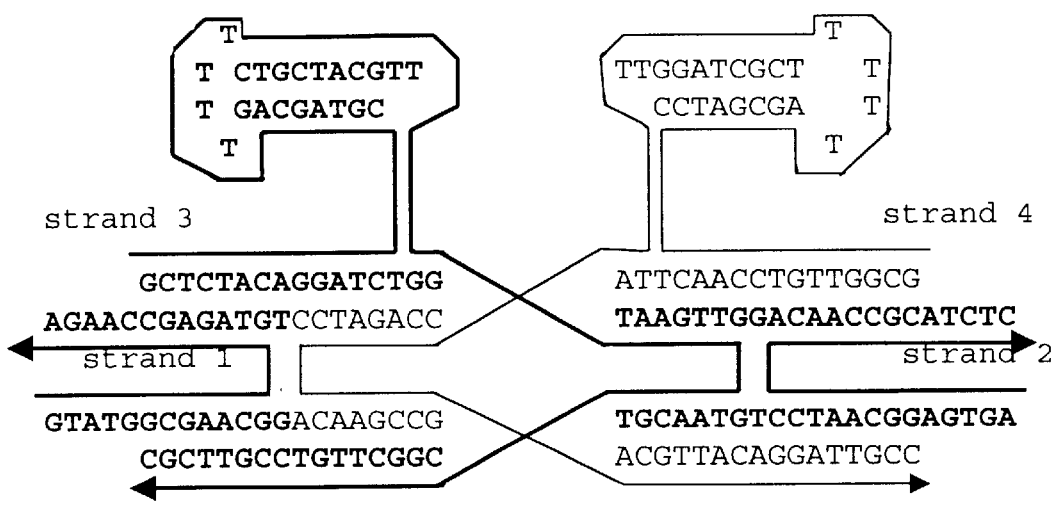
Figure 5H:
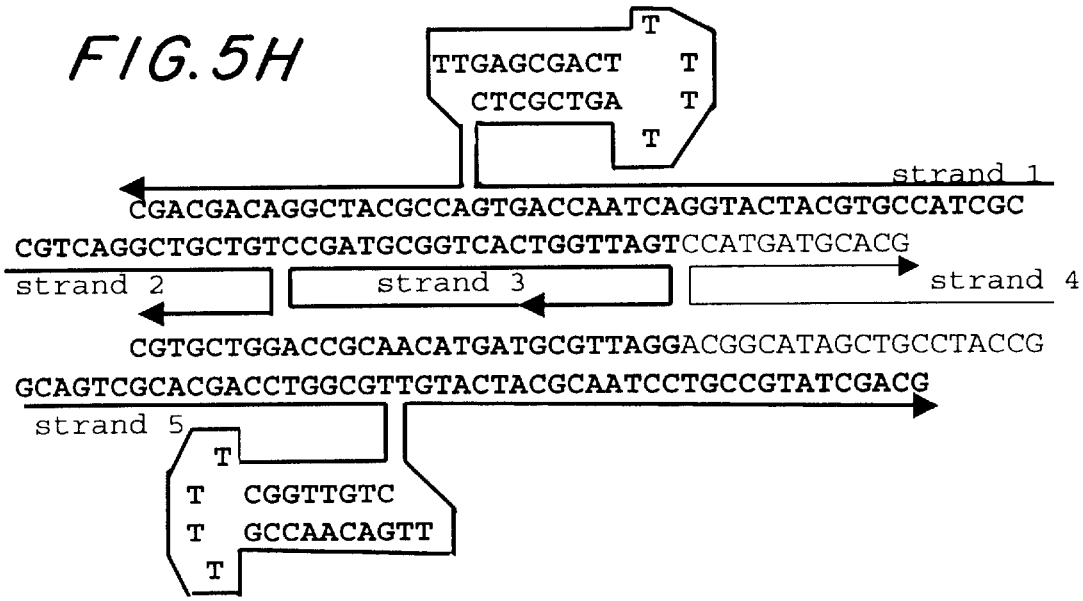

| FIG. 5C | Strand 1 = SEQ ID NO:1 |
|---|---|
| | Strand 2 = SEQ ID NO:2 |
| | Strand 3 = SEQ ID NO:3 |
| | Strand 4 = SEQ ID NO:4 |
| FIG. 5D | Strand 1 = SEQ ID NO:5 |
| | Strand 2 = SEQ ID NO:6 |
| | Strand 3 = SEQ ID NO:7 |
| | Strand 4 = SEQ ID NO:8 |
| | Strand 5 = SEQ ID NO:9 |
| FIG. 5E | Strand 1 = SEQ ID NO:12 |
| | Strand 2 = SEQ ID NO:13 |
| | Strand 3 = SEQ ID NO:10 |
| | Strand 4 = SEQ ID NO:11 |
| FIG. 5F | Strand 1 = SEQ ID NO:14 |
| | Strand 2 = SEQ ID NO:15 |
| | Strand 3 = SEQ ID NO:16 |
| | Strand 4 = SEQ ID NO:17 |
| | Strand 5 = SEQ ID NO:18 |
| FIG. 5G | Strand 1 = SEQ ID NO:12 |
| | Strand 2 = SEQ ID NO:13 |
| | Strand 3 = SEQ ID NO:19 |
| | Strand 4 = SEQ ID NO:20 |
| FIG. 5H | Strand 1 = SEQ ID NO:23 |
| | Strand 2 = SEQ ID NO:15 |
| | Strand 3 = SEQ ID NO:16 |
| | Strand 4 = SEQ ID NO:17 |
| | Strand 5 = SEQ ID NO:27 |

Figure 6:
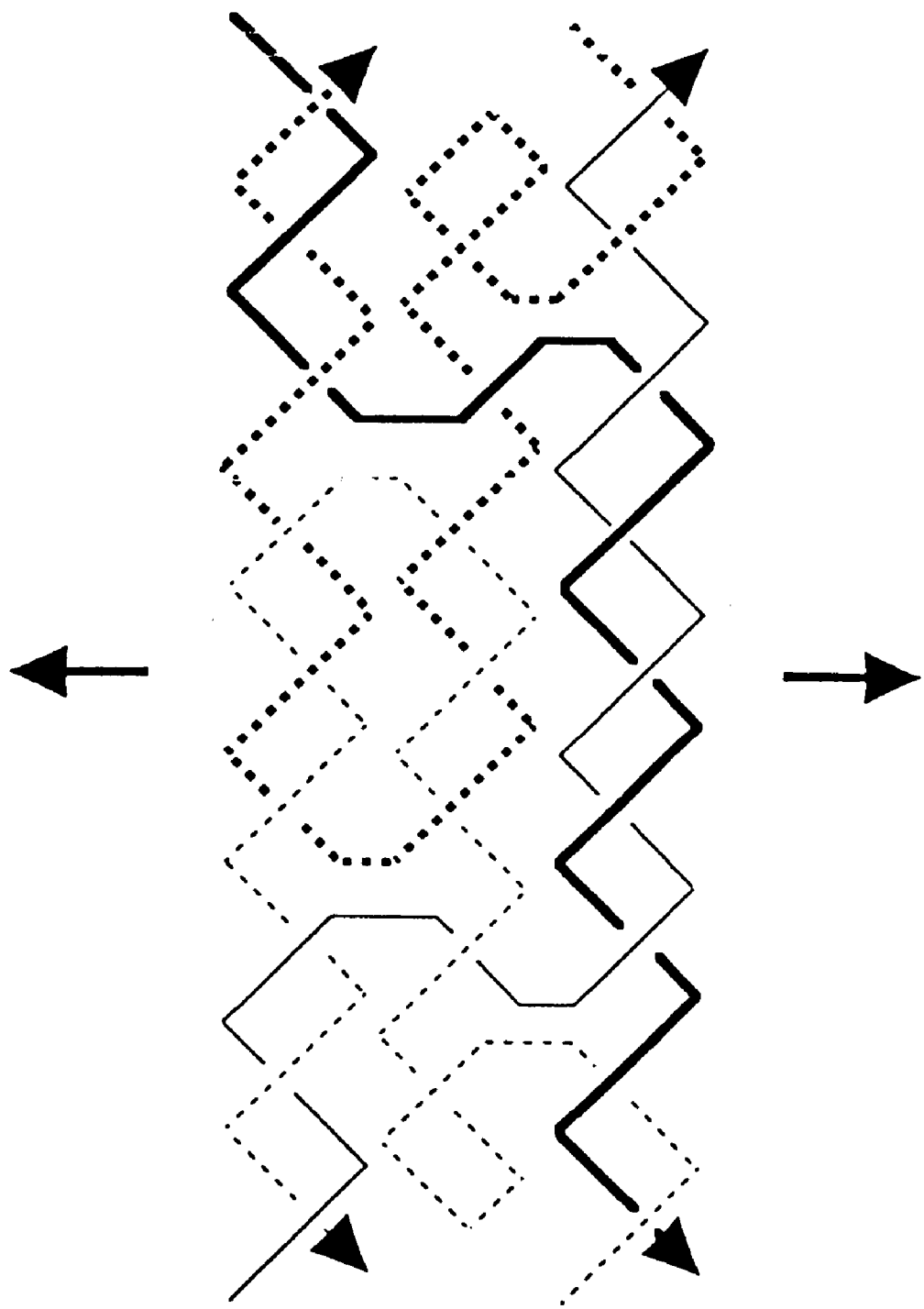

FIG. 6 shows the structure an antiparallel multi-crossover molecule having three double helical domains with parallel helical axes. The four strands of this molecule are represented by solid thin and bold lines and by dashed thin and bold lines.

Figure 7A:
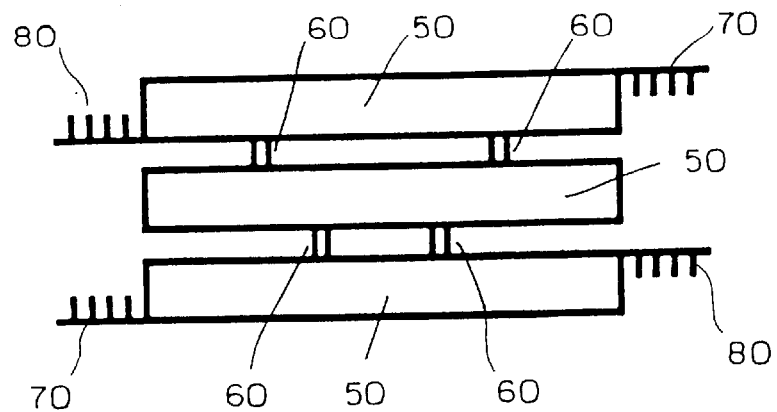
Figure 7B:
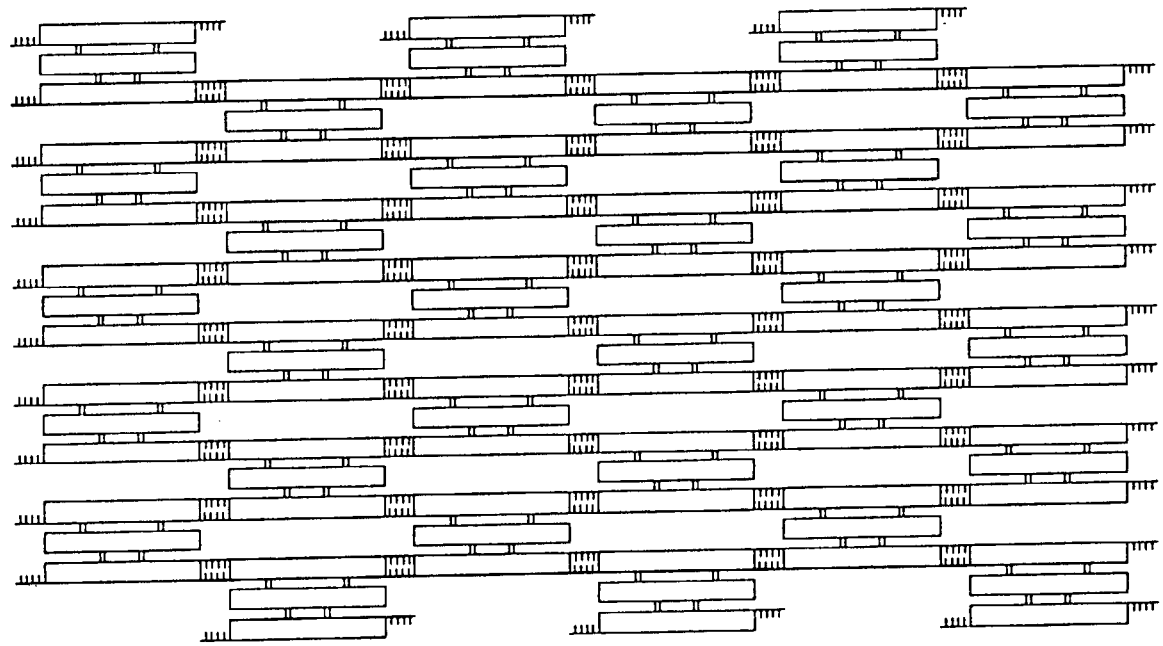

FIGS. 7A and 7B show a schematic representation of the antiparallel multi-crossover molecule having three double helical domains with parallel helical axes of FIG. 6 (FIG. 7A) and an array of such molecules (FIG. 7B).

Figure 8:
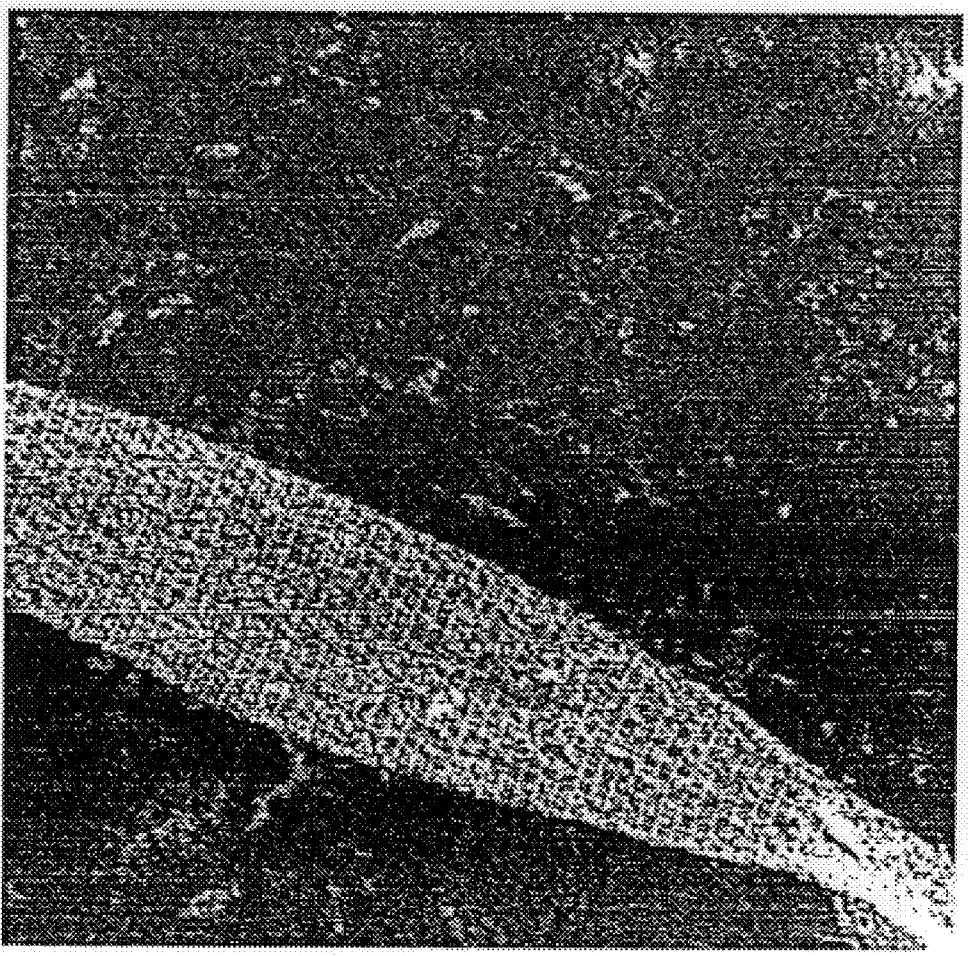

FIG. 8 shows an AFM image of an array of two different antiparallel multi-crossover molecules having three double helical domains with parallel helical axes. One of the molecules is a simple molecule such as shown in FIG. 6, and the other molecule contains the extra hairpins features, as in the AB motif that resulted in the material shown in FIG. 11E below.

FIGS. 9A–9E show the strand structure and sequences used in Example 2. The five molecules used are illustrated in a form that unwinds the helices but permits easy labeling of their DNA sequences. The 3' end of each strand is indicated by an arrowhead. Molecules A (FIG. 9A) and C (FIG. 9D) are DX molecules, and B^ (FIG. 9B), B° (FIG. 9C), and D* (FIG. 9E) are DX+2J molecules. The restriction study uses molecules A, B°, C, and D*, and the ligation study uses molecules A, B^, C, and D*. Molecule B^ contains a recognition site for the restriction endonuclease Pvu II; the points of scission are indicated by filled triangles. Molecule B° is included in the array as just the central molecule containing sticky ends. The hairpins, containing sticky ends complementary to B°, are also shown; these hairpin molecules are ligated to B° in the ligation experiment; other than their hairpins, B^ and B° are identical. Note that the sticky ends are complementary in alphabetical order but that 2.5 turns separate crossover points between molecules. Consequently, the molecules bridge between each other at an interface and thereby tile the plane, rather than forming a simple linear structure. The sequences shown in FIGS. 9A–9E are as follows:

| FIG. 9A | Strand 1 = SEQ ID NO:51 |
|---|---|
| | Strand 2 = SEQ ID NO:52 |
| | Strand 3 = SEQ ID NO:53 |
| | Strand 4 = SEQ ID NO:54 |
| | Strand 5 = SEQ ID NO:55 |
| FIG. 9B | Strand 1 = SEQ ID NO:56 |
| | Strand 2 = SEQ ID NO:57 |
| | Strand 3 = SEQ ID NO:58 |
| | Strand 4 = SEQ ID NO:59 |
| | Strand 5 = SEQ ID NO:60 |
| FIG. 9C | Strand 1 = SEQ ID NO:61 |
| | Strand 2 = SEQ ID NO:62 |
| | Strand 3 = SEQ ID NO:63 |
| | Strand 4 = SEQ ID NO:64 |
| | Strand 5 = SEQ ID NO:65 |
| | Strand 6 = SEQ ID NO:66 |
| | Strand 7 = SEQ ID NO:67 |
| | Strand 8 = SEQ ID NO:68 |
| | Strand 9 = SEQ ID NO:69 |
| FIG. 9D | Strand 1 = SEQ ID NO:70 |
| | Strand 2 = SEQ ID NO:71 |
| | Strand 3 = SEQ ID NO:72 |
| | Strand 4 = SEQ ID NO:73 |
| | Strand 5 = SEQ ID NO:74 |
| FIG. 9E | Strand 1 = SEQ ID NO:75 |
| | Strand 2 = SEQ ID NO:76 |
| | Strand 3 = SEQ ID NO:77 |
| | Strand 4 = SEQ ID NO:78 |
| | Strand 5 = SEQ ID NO:79 |

Figure 10:
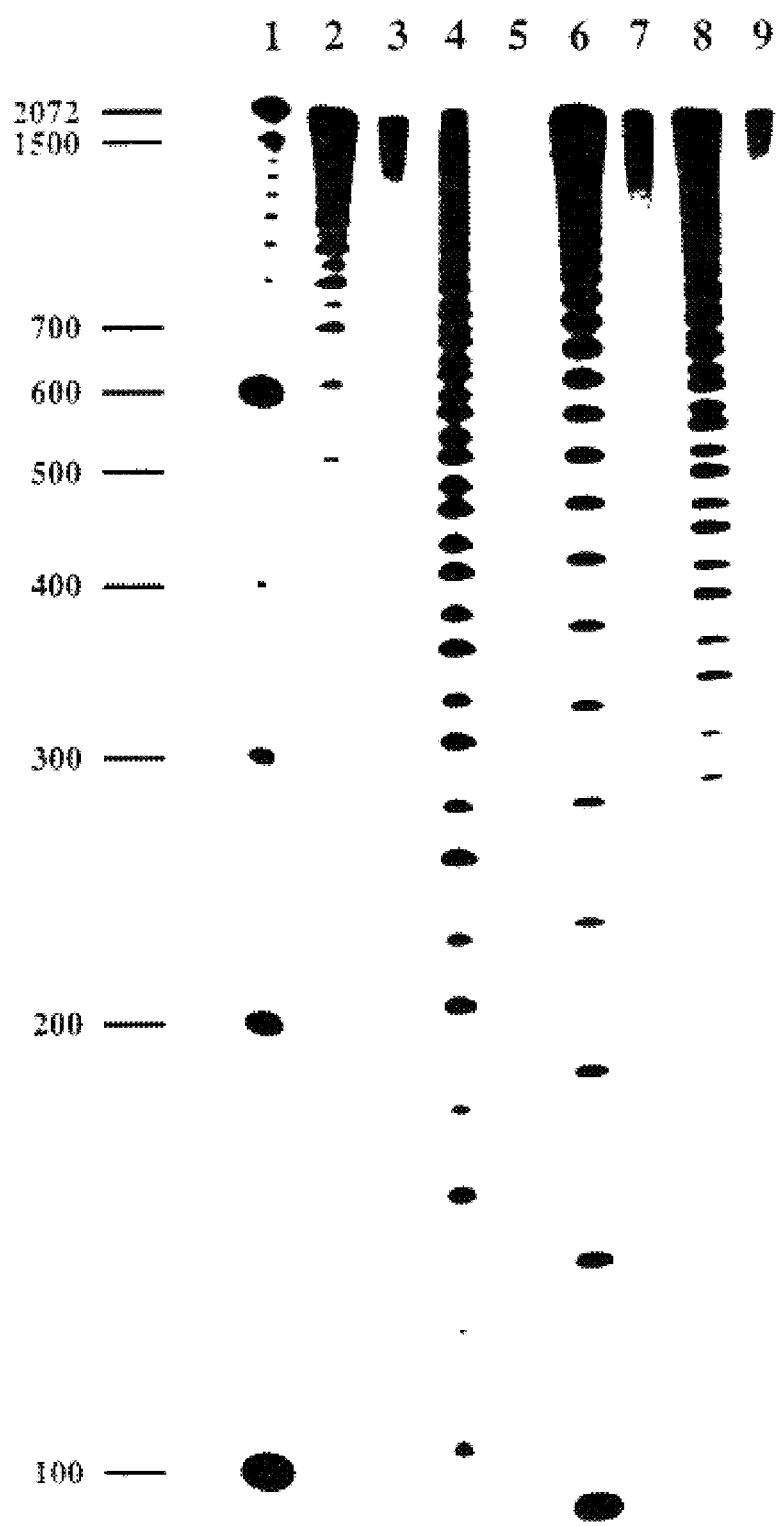

FIG. 10 shows an autoradiogram of a 4% denaturing polyacrylamide gel showing the product after assembly of 2-D lattice DAE-O (type AB), ligation to form long covalent strands, and denaturing to separate the strands. Lane 1 contains a ladder of markers at 100 base intervals. In the remaining lanes, a different strand from unit B is labelled: lanes 2 and 3 correspond to red strands (FIG. 2D), lanes 4 and 5 are green strands, lanes 6 and 7 are blue strands, and lanes 8 and 9 are yellow strands. *E. coli* exonucleases I and III were added to the material in the odd-numbered lanes to degrade single stranded species, thus showing that no circular products were formed.

Figure 11A:
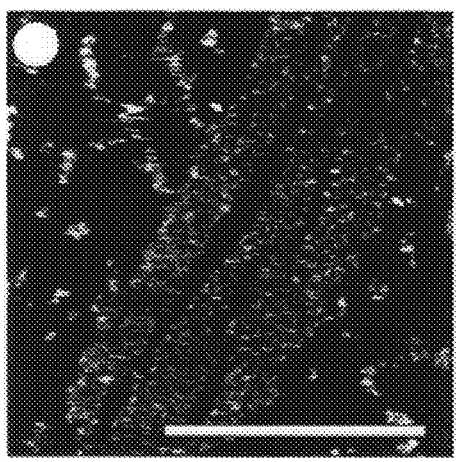
Figure 11D:
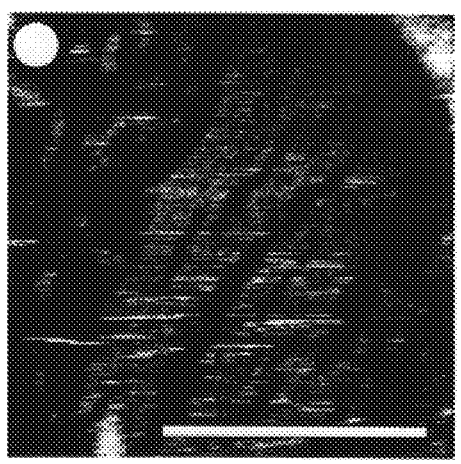
Figure 11B:
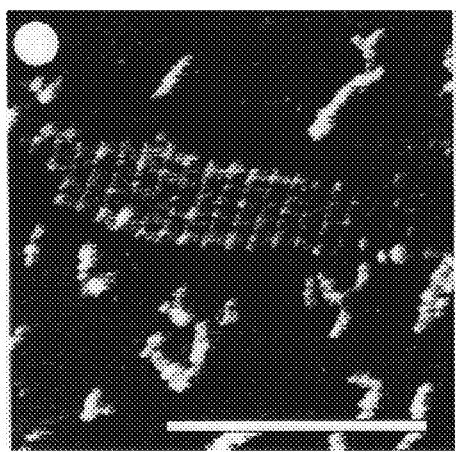
Figure 11E:
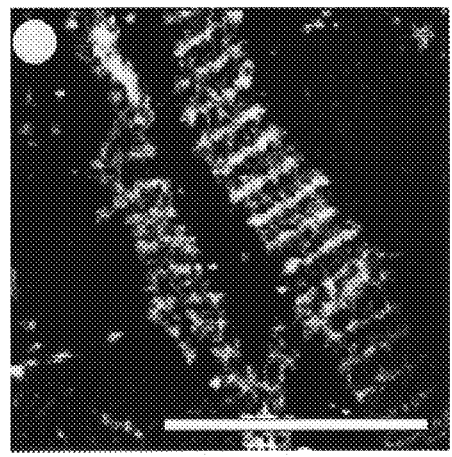
Figure 11C:
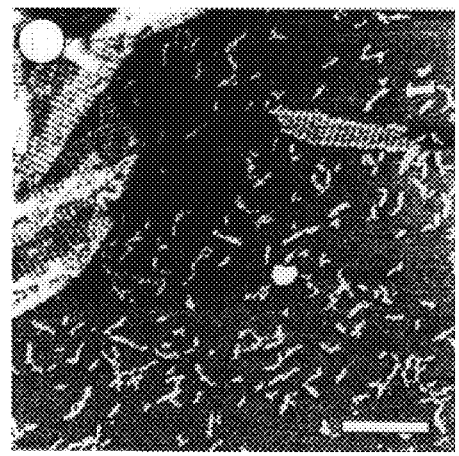
Figure 11F:
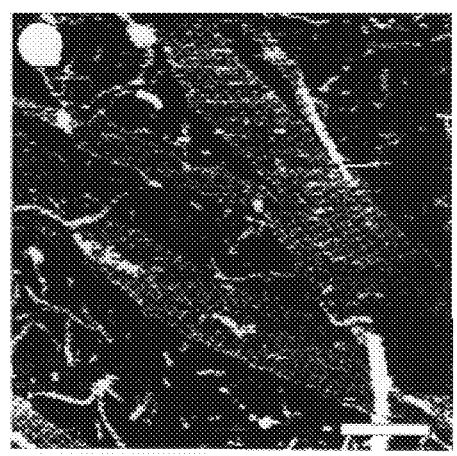

FIGS. 11A–11F show AFM images of two-unit lattices. FIG. 11A shows a DAO-E AB lattice. A possible vertical column is indicated by the arrows. Fourier analysis shows 13±1 nm periodicity; each DAO is 12.6 nm wide. FIGS. 11B and 11C show a DAO-E AB' lattice (two views of the same sample). Stripes have 25±2 nm periodicity; the expected value is 25.2 nm. FIG. 11D shows a DAE-O AB lattice. FIGS. 11E and 11F show DAE-O AB' lattice (different samples, see Materials and Methods section in Example 1). Stripes have 33±3 nm periodicity; the expected value is 32 nm. All scale bars are 300 nm; images show 500×500 nm or 1.5×1.5 μm. The grayscale indicates height above the mica surface where the apparent lattice height is between 1 and 2 nm.

Figure 12A:
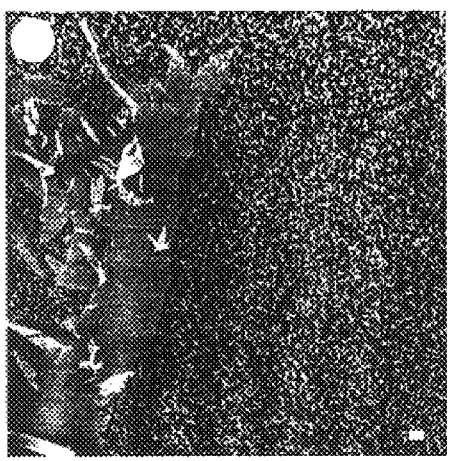
Figure 12D:
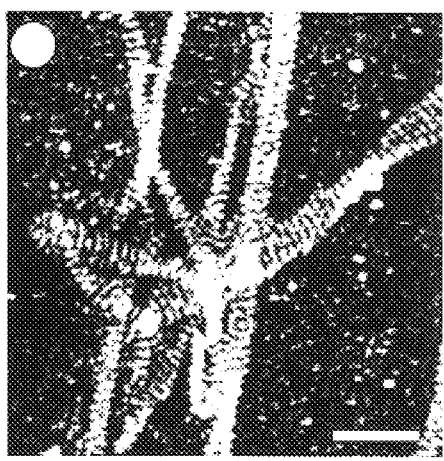
Figure 12B:
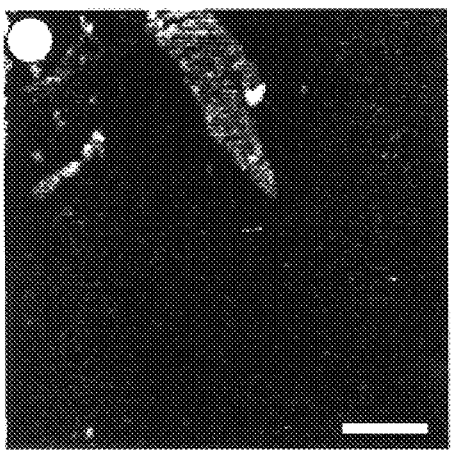
Figure 12E:
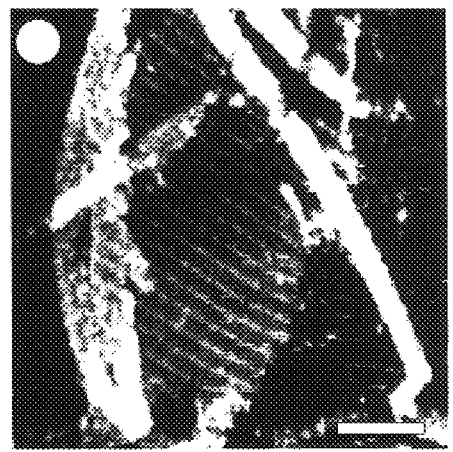
Figure 12C:
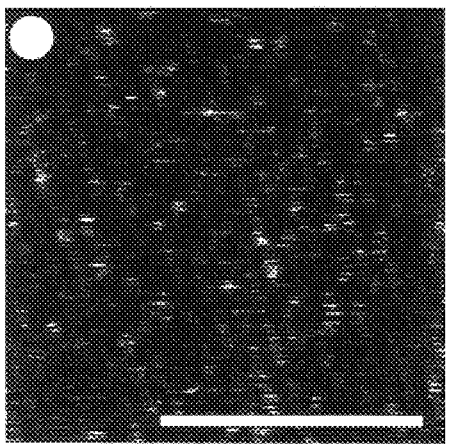
Figure 12F:
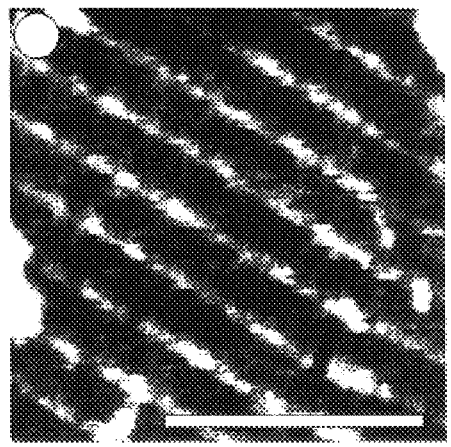

FIGS. 12A–12F show AFM images showing large crystals and modifications of lattice periodicity and surface features. FIGS. 12A–12C show DAO-E AB' lattice at three levels of detail (all the same sample). The largest domain is roughly 2×8 μm, and contains roughly 500,000 double crossover units. FIG. 12D shows the DAE-O AB lattice in which B has been labelled with biotin-streptavidin-nanogold. DAE-O ABCD' lattice is shown in FIGS. 12E and 12F at two levels of detail (the same sample). Stripes have 66±5 nm periodicity; the expected value is 64 nm. All scale bars are 300 nm; images show 500×500 nm, 1.5×1.5 μm, or 10×10 μm. The grayscale indicates height above the mica surface where the apparent lattice height is between 1 and 2 nm.

FIGS. 13A–13D show restriction of crystalline array (FIG. 13B) and ligation or hydrogen bonded annealing to a crystalline array (FIG. 13D) with the four components of each array shown schematically in FIG. 13A and FIG. 13C, respectively. The four tiles are labeled, and each is shaded differently. In FIG. 13C, the sticky ends are shown as complementary geometric shapes. A and C are DX molecules, and B^ and D* are DX+2J molecules. Their protruding hairpins are represented by filled circles. The different circle fillings indicate that the hairpins differ between the two DX+2J molecules. The topographic features of the DX+2J molecules appear as stripes (vertical rows of filled circles) in the AFM, whose resolution is sufficient to resolve stripes but insufficient to resolve individual hairpins packed together with 4 nm spacings. The bottom part of FIG. 13B illustrates the effect of removing the hairpin of B^ by restriction: the prominent stripe is replaced with a much less intense feature. In FIG. 13D, the same conventions apply as in FIG. 13B. The difference here is that B° replaces B^. This component contains short arms ending in sticky ends that do not produce an intense feature in the AFM. The drawing illustrates that the addition of hairpins to this array produces a pattern similar to the starting pattern of FIG. 13B. Annealing and ligation produce the same results, although the sticky ends used for annealing are longer.

Figure 14A:
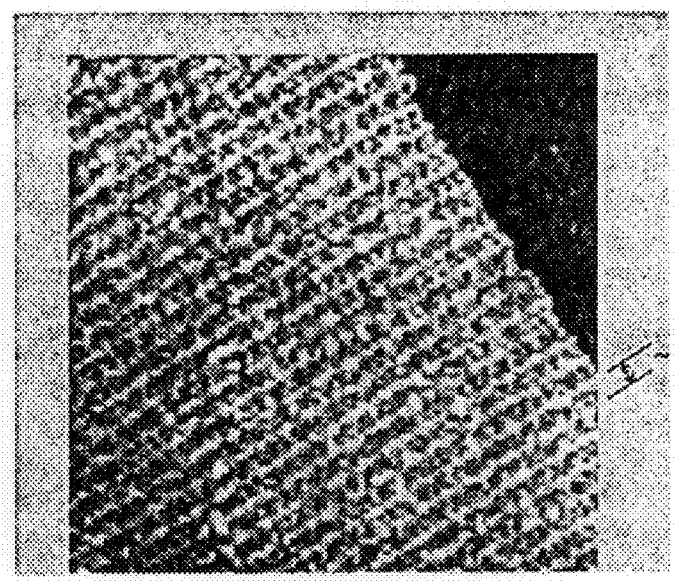
Figure 14B:
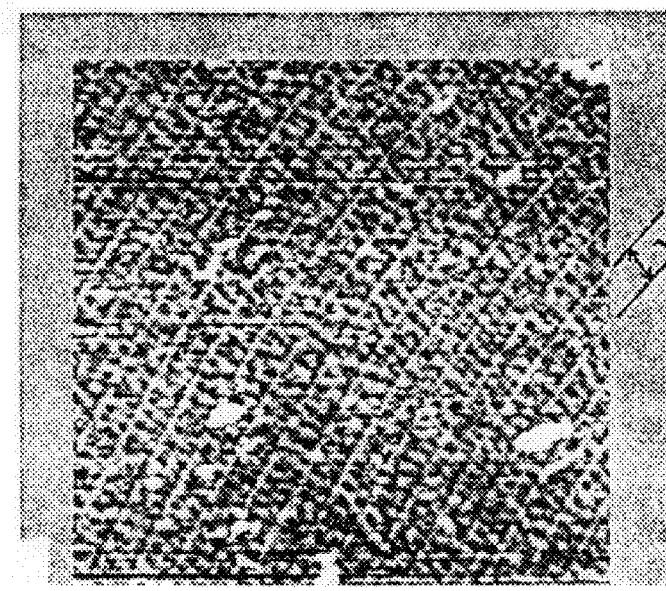

FIGS. 14A and 14B show AFM images illustrating the restriction of a 2D crystal. The array before restriction is shown in FIG. 14A. Prominent stripes are visible in this image. These result from the DX+2J motifs of the B^ and D* components of the array. Individual hairpins are not resolved in the narrow direction of the molecules (ca. 4 nm). The spacing between the stripes is shown to be about 32 nm, the expected distance for nine turns of DNA. The array after restriction is shown in FIG. 14B. The spacing of the prominent stripes is seen to double to about 64 nm. This is consistent with removal of the B^ hairpins, while retaining the D* hairpins. Weaker stripes are visible halfway between the prominent stripes, perhaps resulting from the residual arms on B^ following restriction. There is a certain amount of debris visible, but the array appears undamaged.

Figure 15A:
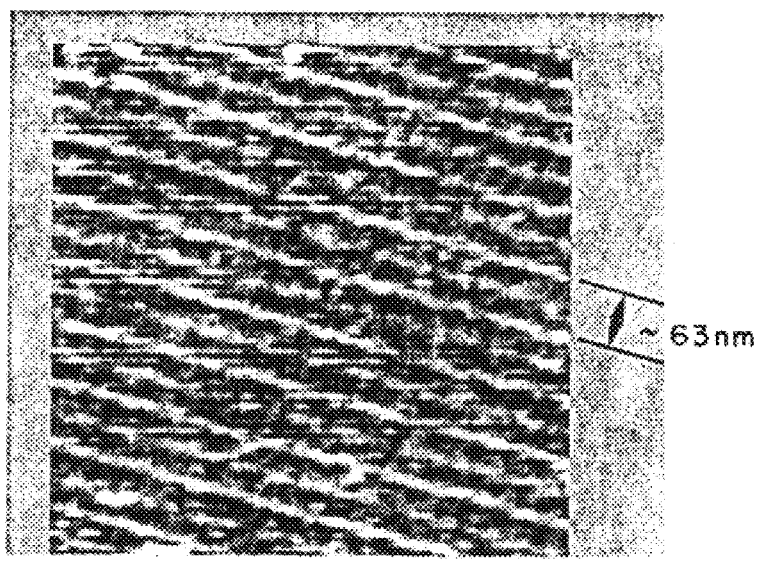
Figure 15B:
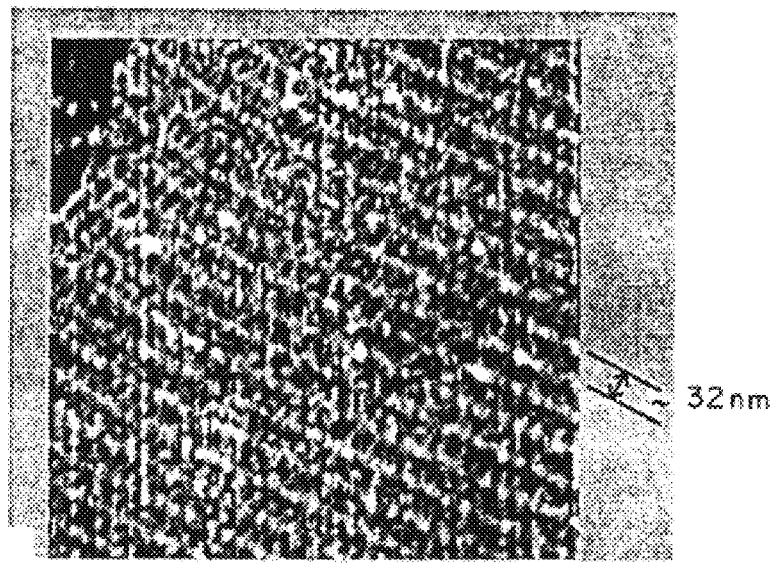

FIGS. 15A and 15B show AFM images illustrating the modification of a two dimensional crystal by ligation. A crystal before ligation is shown in FIG. 15A. Prominent stripes are apparent in this large array. Less prominent stripes are visible halfway between these stripes, similar to the image seen in FIG. 14B. The spacing of the prominent stripes is about 63 nm, the expected distance for 18 turns of DNA. A crystal after ligation is shown in FIG. 15B. This image shows a series of uniformly spaced stipes of equal prominence, in contrast to FIG. 15A, where the stripes alternated in intensity. The spacing of the stripe seen clearly in this view is about 32 nm, the expected distance if the ligation has been successful in adding the hairpins to B°.

Figure 16A:
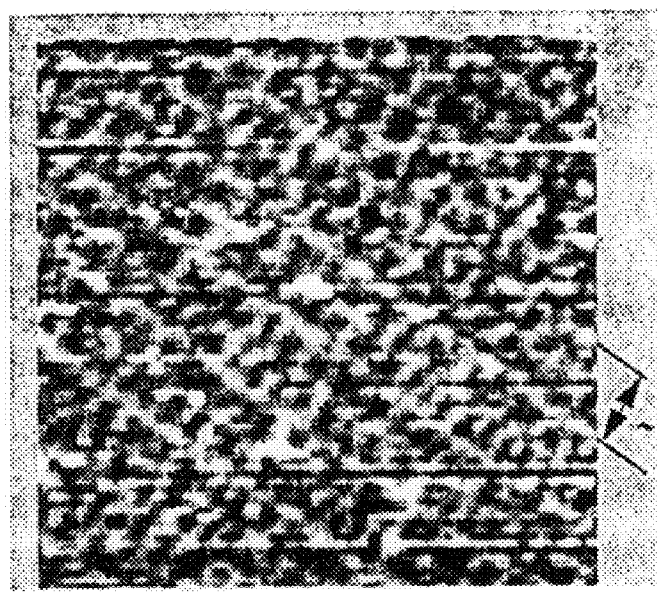
Figure 16B:
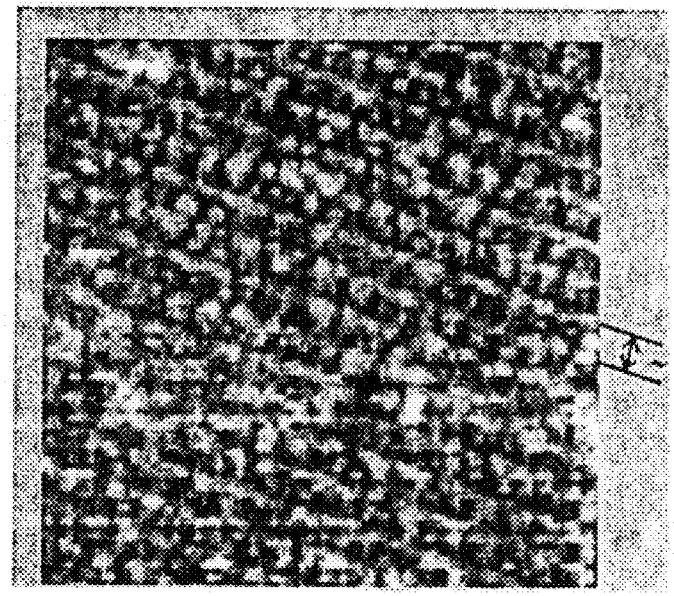

FIGS. 16A and 16B show AFM images illustrating the modification of a two dimensional crystal by hydrogen bonding. A crystal before hydrogen bonding is shown in FIG. 16A. Similar to FIGS. 15A and 15B, an array containing prominent stripes with a separation of ~64 nm is seen; weaker stripes alternate with the prominent ones, halfway between them. A crystal after hydrogen bonding is shown in FIG. 16B. Both stripes are equally prominent, and they are separated by ~32 nm.

DETAILED DESCRIPTION OF THE INVENTION

The periodic polynucleic acid structures of the present invention are based on the discovery that antiparallel DNA double crossover molecules, approximately 2×4×13 nm or 2×4×16 nm in size, self-assemble in solution to form single domain crystals as large as 2×8 microns with uniform thickness between 1 and 2 nm, as visualized by atomic force microscopy (AFM). Thus, single-stranded oligonucleotides or polynucleotides self-assemble to form two-dimensional polynucleic acid structures composed of multimers of repeating units of at least two antiparallel DNA double crossover molecules. Three-dimensional structures can also be either self-assembled or assembled as extensions of preformed two-dimensional structures.

The laboratories of the present inventors also created specific lattices with programmable structures and features on the nanometer scale. A hairpin was incorporated into an antiparallel double nucleic acid double crossover molecule (DX) to serve as a topographic label for visualization by AFM, producing observable stripes above the surface at predictable intervals of 25, 32 and 64 nm. Two-component lattices have been assembled with a stripe every other unit, and by programming cohesive or sticky-ended associations differently, four-component lattices have been produced with a stripe every fourth unit.

DNA molecules containing two crossover sites between helical domains have been widely suggested as intermediates in recombination processes involving double strand breaks. Accordingly, "double crossover molecules" (DX) are those nucleic acid molecules containing two branched junctions (Holliday junctions corresponding to the crossover sites) linked together by ligating two of their double helical arms. By "branched junction" is meant a point from which three or more helices (arms) radiate.

There are five isomers of double crossover molecules (Fu et al, 1993) which fall into two broad classes of molecules differentiated by the relative orientations, parallel (DP) or antiparallel (DA), of their helix axes. Antiparallel isomers of double crossover molecules, which are the only isomers stable in small molecules, are used in Examples 1 and 2 below.

Figure 1A:
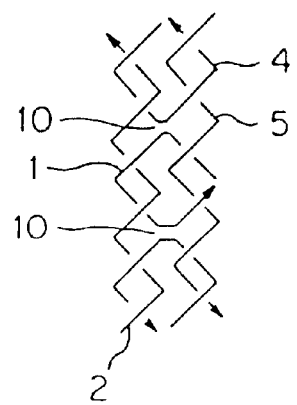
FIGS. 1A–1C show a schematic representation of two types of antiparallel double crossover molecules, DAE (FIG. 1A), with an even number of double helical half-turns between the crossover, and DAO (FIG. 1B), with an odd number of half-turns between the crossovers and of a DAE molecule having two extra hairpin loops included in the helical strands at sites of bulged three-arm junctions (FIG. 1C) and which is derived from DAE and designated as DX+2J. The DAE molecule as illustrated contains five strands, two of which are continuous, or helical strands, drawn with thick lines, and three of which are crossover strands, drawn with thin lines, including the cyclic strand in the middle. The 3' ends of each strand are indicated by an arrowhead. The DAO molecule is depicted to the right of the DAE molecule, and it contains only 4 strands. Two of these are drawn with thick lines and two with thin lines. The twofold symmetry element is perpendicular to the page for the DAE molecules, and it is horizontal within the page, for the DAO molecule. Thick lines are symmetrically related to thick lines and thin to thin lines by symmetry in the DAO molecule. Sealing the cyclic strand in the middle of the DAE molecule would be necessary for the symmetry to be exact for that molecule. In the DX+2J molecule (FIG. 1C), the two loops are drawn to protrude out of the plane of the DAE helix axes: the one on the right, drawn with a very thin line, goes into the page, and the one on the left, drawn with a very thick line, comes out of the page. These hairpins act as topographic markers that are visible in the AFM.
Figure 1B:
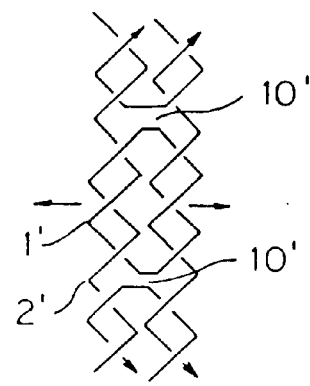
Figure 1C:
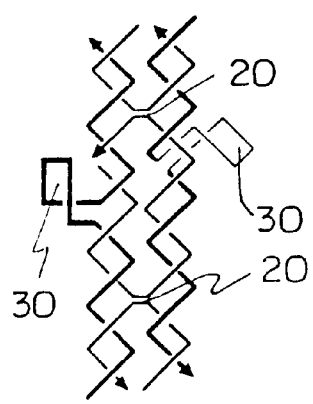

In order to avoid torsional stress on the double crossover molecules, the distance between the branched junction or crossover points is specified as either even (E) or odd (O) multiples of half helical turns. Antiparallel double crossover molecules with an even number of half helical turns between crossover points are designated DAE and those with an odd number are designated DAO. FIGS. 1A and 1B show schematic representations of the DAE and DAO forms, respectively, of antiparallel double crossover molecules in which two strands of a helix are presented as a pair of thick and thin lines. The DAE and DAO molecules depicted in FIGS. 1A and 1B have strands 1, 2, 4 and 5 and strands 1' and 2' respectively. There are two half helical turns between the two crossover points (10) in the DAE molecule depicted and three half helical turns between crossover points (10') in the DAO molecule. FIG. 1C depicts a double crossover molecule (DX), derived from a DAE molecule with four half-turns between crossover points (20), having two extra hairpin loops (30) included in the helical strands at the sites of bulged three-arm junctions.

Figure 2B:
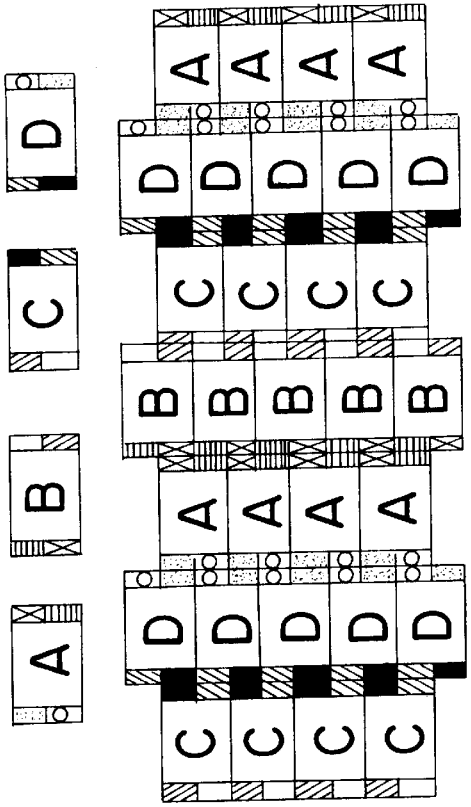
FIGS. 2A–2D illustrate two embodiments of double crossover molecular structures into 2-D lattices. The logical structure for 2-D lattices consisting of two units and four units are presented in FIGS. 2A and 2B, respectively. In the two unit design (FIG. 2A), type A units have four colored edge regions (represented by solid, dashed, hatched, etc. areas on the edges of the tiles), each of which match exactly one colored region of the adjacent type B units. Similarly, in the four unit design (FIG. 2B), the edge colors are chosen uniquely to define the desired relations between neighboring tiles. Note that rotations and reflections of Wang tiles are disallowed; an equivalent restriction could also be obtained by using non-rectangular tiles or more complex patterns of colors.
Figure 2A:
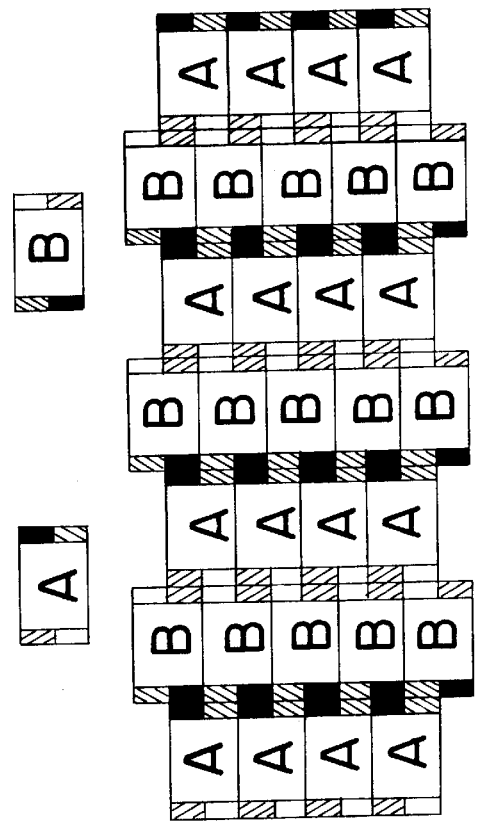

The two-dimensional crystal design according to the present invention is derived from the mathematical theory of tiling (Grunbaum, 1986; Winfree, 1996). The desired lattice is specified by a set of Wang tiles with colored edges; the Wang tiles may be placed without rotation next to each other only if their edges are identically colored (as represented by solid, dashed, hatched, etc. edge areas) where they touch (FIGS. 2A and 2B). Synthetic molecular units corresponding to these tiles are designed, such that they will self-assemble into a crystal that obeys the coloring conditions. In DNA, two adjacent colored edge portions of two tiles correspond to two complementary sticky ends. As an initial demonstration of molecular Wang tiles, the simplest non-trivial set of tiles: two tiles, A and B, which make a striped lattice (FIG. 2A) was chosen (the simplest set of tiles, however, is a set of single tiles AA which are placed next to each other in the alternating manner of A and B tiles shown in FIG. 2A). The set of tiles represent a repeating unit of at least two antiparallel nucleic acid multi-crossover molecules in a lattice. The term "at least two antiparallel nucleic acid multi-crossover molecules" is meant to be a plurality of a single molecular species, e.g., AA, or more than one molecular species, e.g., AB, ABCD, etc. A set of four tiles which produce a striped lattice with a greater period is also presented in FIG. 2B. Other periodic lattices of tiles, such as three tiles (e.g., ABCA) or six tiles, etc. can also be produced, although odd numbers of tiles in the pattern may require different individual units. Translated into molecular terms, DX systems that self-assemble in solution into two-dimensional crystals with a well-defined subunit structure are obtained.

The antiparallel DX motif (Fu et al, 1993) consists of two juxtaposed immobile 4-arm junctions (Seeman, 1982) arranged such that at each junction the non-crossover strands are antiparallel to each other. The design depends critically upon the twist of the B-form DNA double helix, in which a full turn takes place in ≈10.5 base pairs (J. C. Wang, 1979; Rhodes et al, 1980). DAO molecules have an odd number of half turns (e.g., three half turns is ≈16 pairs) between crossover points, while DAE molecules have an even number of half turns (e.g., four half turns is ≈21 base pairs). Computer models of the DX molecules used in Example 1 are shown in FIGS. 5A and 5B. The DAO molecules consist of 4 strands of DNA, each of which participates in both helices. The DAE molecules consist of 3 strands that participate in both helices, and 2 strands that do not cross over. Each corner of each DX unit has a single-stranded sticky (cohesive) end with a unique sequence; specific association of DX units is controlled by choosing sticky ends with Watson-Crick complementarity.

To ensure that the component strands form the desired complexes, strand sequences are designed carefully so that alternative associations and conformations are unlikely. Therefore, the "negative design problem" (Seeman, 1990; Yue et al, 1992; Sun et al, 1996) for DNA is solved, where sequences are found that maximize the free energy difference between the desired conformation and all other possible conformations. The principle of sequence symmetry minimization (Seeman, 1982; Seeman, 1990) is used to optimize the sequences and to minimize the length and number of unintentional Watson-Crick complementary subsequences. In each DX molecule's sequences, there are no six base subsequences complementary to other six base subsequences except as required by the design, and spurious five base complementarity is rare. Thus, it is expected that during self-assembly, the DNA strands spend little time in undesired associations and form DX units with high yield.

Figure 2C:
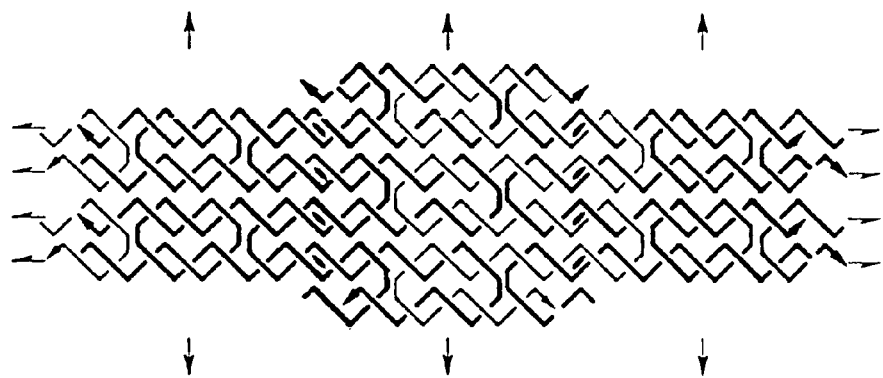
Figure 2D:
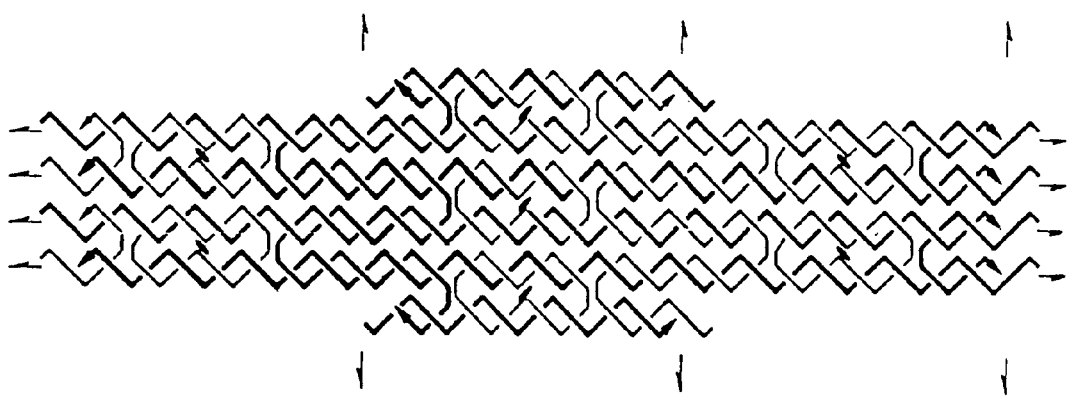

DX units can be designed that will fit together into a two-dimensional crystalline lattice. Either two or four distinct unit types (FIGS. 2A and 2B) are used to produce striped lattices. To implement the two-unit lattice, two separate systems can be used, one consisting of two DAO units, the other consisting of two DAE units. The lattices produced by these systems are called DAO-E and DAE-O, respectively, to indicate the number of half-turns between crossover points on adjacent units and their distinct topologies are shown in FIGS. 2C and 2D. Covalently joining adjacent nucleotides at nicks in the lattice, by chemical or enzymatic ligation, would result in a "woven fabric" of DNA strands. Ligation of DAO-E design produces four distinct strand types, each of which continues infinitely in the vertical direction (as used herein "vertical" and "horizontal" will always be as in FIGS. 2C and 2D). The DAE-O design involves two small nicked circular strands in addition to four infinite strands, two of which extend horizontally and two of which extend vertically (FIG. 2D). The DAO-E design has the advantage of using simple 4-strand DX units, while in the DAE-O design, the horizontal and vertical strands can serve as reporters for the extent of self-assembly if the molecules are ligated and analyzed by gel electrophoresis.

As used here, a reporter strand is a strand of nucleic acid whose fate in a test or assay represents the fate of the entire nucleic acid molecular complex (i.e., lattice). Likewise, if the molecular complex were to cyclize, the reporter strand would also cyclize. Thus, the reporter strand provides the advantage whereby it is much easier to characterize the fate of the molecular complex by the fate of the reporter strand than by the entire complex itself.

Control of self-assembly to yield the 2-D lattice is obtained by two design criteria. First, the sticky-end (cohesive) sequences for each desired contact are unique; this ensures that the orientations and adjacency relations of the DX units comply exactly with the design in FIGS. 2A and 2B. Sticky/cohesive ends are lengths 5 and 6 for the DAO-E and DAE-O designs respectively, so that each correct contact contributes approximately 8 or 14 kcal/mol to the free energy of association at 25° C., according to a nearest-neighbor model (SantaLucia et al, 1996). Second, the lengths of the DX arms and sticky/cohesive ends, and thus the separations between crossover points, respect as closely as possible the natural twist of the B-form DNA double helix. The adjacent DX molecules are effectively coupled by torsional springs whose equilibrium positions have been designed to keep the adjacent DX molecules coplanar.

Figure 3A:
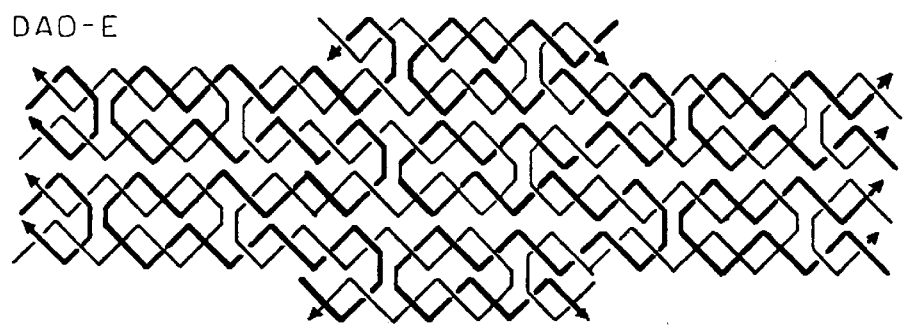
FIGS. 3A–3D show lattice topologies produced by DAO-E (FIG. 3A) and DAO-O (FIG. 3B), each with three half-helical turns between crossover points, and by DAE-O (FIG. 3C) and DAE-E (FIG. 3D), each with two half turns between crossover points. Arrowheads indicate the 3' ends of strands.
Figure 3B:
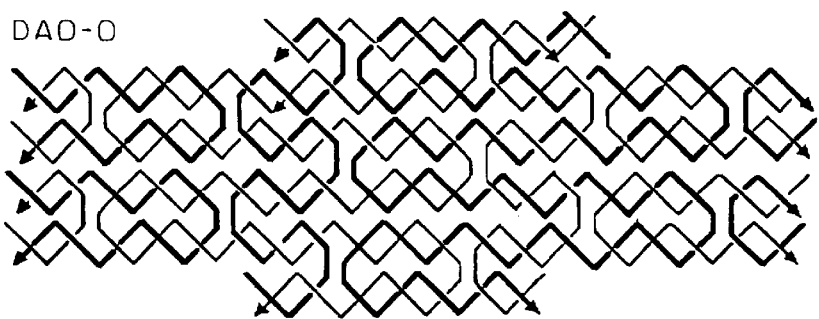
Figure 3C:
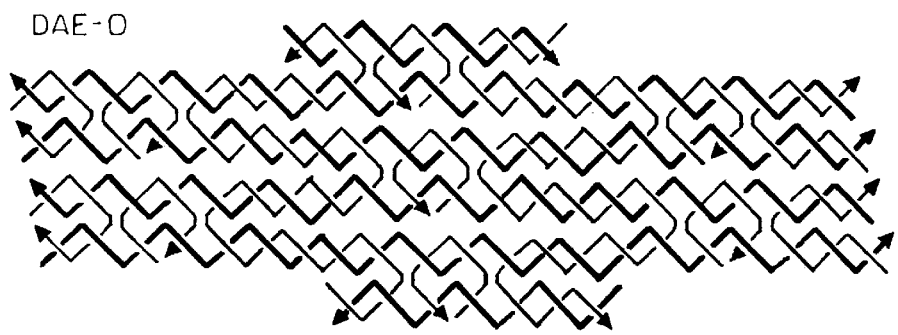
Figure 3D:
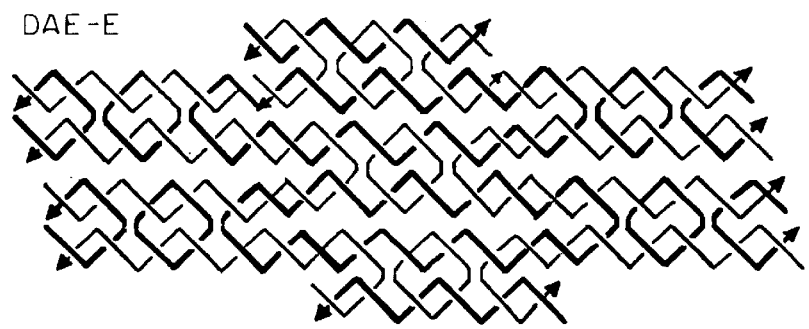

The separation between crossover points can be varied by multiples of half turns of the parallel helices (the axes of the helices are parallel) in antiparallel double crossover (DX) or multi-crossover molecules (where an odd number of half turns for DX molecules form DAO molecules and an even number of half turns for DX molecules form DAE molecules) to maintain at least the DX molecules coplanar according to the present invention. To illustrate with DX molecules, the DAE molecules forming the DAE-O lattice shown in FIG. 2D have four half-helical turns between their crossover points and five between crossover points on adjacent units, whereas the DAE molecules forming the DAE-O lattice shown in FIG. 3C have two half turns between their crossover points and five half turns between crossover points on adjacent units.

The antiparallel nucleic acid crossover molecules forming the adjacent repeating units of the lattice according to the present invention are not limited to double crossover molecules. They are multi-crossover molecules with two or more crossover sites and includes any DNA molecule in which two or more double helical domains are linked by crossover strands more than once. However, when more than two crossover sites are present, it will be appreciated by those of skill in the art that the number of half turns between each pair of adjacent crossover sites are designed to maintain the antiparallel nucleic acid multi-crossover molecule coplanar (at least for double crossover molecules), and importantly, to maintain a two-dimensional lattice of adjacent antiparallel multi-crossover molecule in the same plane. Each antiparallel nucleic acid multi-crossover molecule, having two or more adjacent double helical domains with helix axes in parallel, is connected to an adjacent antiparallel nucleic acid multi-crossover molecule by complementary cohesive ends to form an extended double helical domain between a first double helical domain of a first antiparallel nucleic acid multi-crossover molecule and a second double helical domain of an adjacent antiparallel nucleic acid multi-crossover molecule. However, the corresponding second double helical domain of the first antiparallel nucleic acid multi-crossover molecule is not colinear and connectible to form a second extended double helical domain with the first double helical domain of the same adjacent antiparallel nucleic acid multi-crossover molecule. Rather, the corresponding second double helical domain of the first antiparallel nucleic acid multi-crossover molecule is colinear and connectible to form a second extended double helical domain with a first double helical domain of a different adjacent antiparallel nucleic acid multi-crossover molecule. In this way, an extended two-dimensional array or lattice is generated. Furthermore, each repeating unit is connected to an adjacent repeating unit in the same plane to form at least one extended double helical domain between adjacent repeating units in the same plane.

Figure 4:
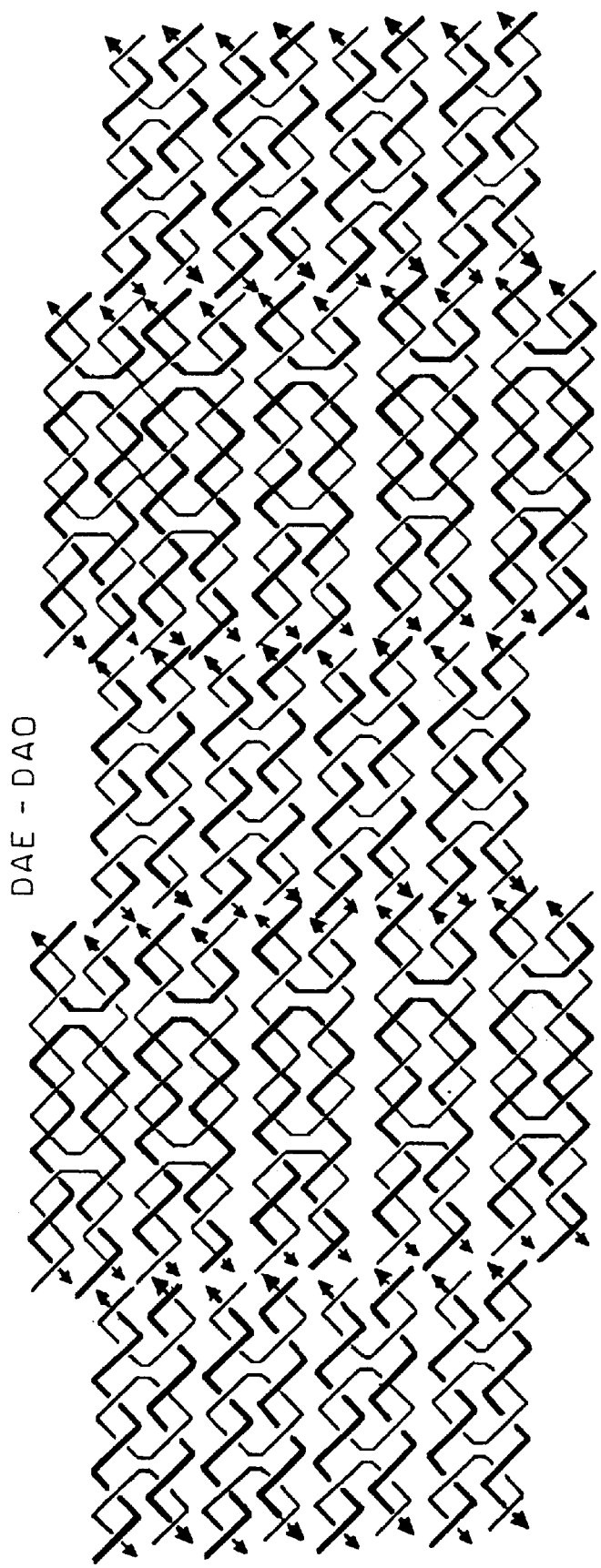
FIG. 4 shows a lattice topology produced by alternating DAE and DAO molecules.

While the two components in the lattices shown in FIGS. 2C and 2D are either both DAO molecules or DAE molecules, the present invention is not so limited. Multi-component lattices can be designed to be a mixture of DAO and DAE component molecules as long as the molecules and lattice formed are coplanar. FIG. 4 provides a non-limiting example of a two-component lattice composed of alternating DAE and DAO molecules.

In addition to double crossover and multi-crossover molecules with two double helical domains, this system can also utilize molecules containing more than two double helical domains, such as preferably, but not limited to, three, four or six double helical domains for assembling the periodic polynucleic acid structure according to the present invention. For instance, a third helical domain may be pointing out of the plane formed by the first and second helical domains of an antiparallel nucleic acid multi-crossover molecule or its helix axis may be parallel to the helix axes of the first and second helical domains. As an example of a third double helical domain whose helix axis is parallel to the helix axes of the first and second domains, FIG. 6 shows the strand structure of such an antiparallel nucleic acid multi-crossover molecule having three helical domains with parallel helix axes. Accordingly, as used herein, an antiparallel nucleic acid multi-crossover molecule contains two or more double helical domains, in which the helix axes are parallel and in which adjacent double helical domains are joined by two or more crossovers. A crossover is normally made of two strands that pass between helical domains, although one strand of each pair could, in principle, be nicked.

FIG. 7A depicts a schematic representation of the antiparallel nucleic acid multi-crossover molecule of FIG. 6 with three parallel helical domains (50) connected by double crossovers (60). In this molecule with three double helical domains, the first double helical domain is connected to the second by two or more crossovers and the second is connection to the third by two or more crossover. Two of the helical domains shown in FIG. 7A have cohesive ends (70) and (80) which can anneal with complementary cohesive ends to form an extended two dimensional lattice or array as shown in FIG. 7B. Because the central helical domain shown in FIG. 7B is capped with a hairpin (no free cohesive end), there are 2 nm×~15 nm gaps in the two dimensional lattice of FIG. 7B. These gaps can be filled by using another antiparallel nucleic acid multi-crossover molecule having three helical domains with parallel helix axes and inserting it a non-integral number of base pairs away from the nearest crossover. Although the data in the form of AFM images are not shown for such a filled lattice or array, it was demonstrated that when a distance from the nearest crossover of a turn plus 3 base pairs was used, the antiparallel nucleic acid multi-crossover molecule inserted to fill the gap was rotated about 100 degrees from the plane of the array.

When the antiparallel nucleic acid multi-crossover molecule has four or more helical domains, there are alternate arrangements to the arrangement where these domains have coplanar helix axes such that the first double helical domain is connected by crossovers to the second double helical domain, the second helical domain is connected by crossovers to the third double helical domain, and the third helical domain is connected by crossovers to the fourth double helical domain. An alternate arrangement would be cyclical, where the fourth double helical domain is also connected to the first helical domain to cyclize the helical domains with parallel helical axes. Still another alternate arrangement would be an arrangement in which one double helical domain is a central domain, centrally disposed and connected by crossovers to each of the other three flanking (adjacent) double helical domains. Both alternate arrangements would not have coplanar helix axes. It will be appreciated by those of skill in the art that planarity of the helix axes taken in sets of three or more helical domains is not a requirement. As a further example, a set of six helical domains with parallel helix axes in an antiparallel nucleic acid multi-crossover molecule may be arranged cyclically with hexagonal symmetry, so that the first double helical domain is connected by crossovers to the adjacent second double helical domain, the second double helical domain is connected to the third double helical domain, the third double helical domain is connected to the fourth double helical domain, the fourth double helical domain is connected to the fifth double helical domain, the fifth double helical domain is connected to the sixth double helical domain, and the sixth double helical domain is connected to the first double helical domain, where all connections are crossovers.

FIGS. 5C–5H show the DX units and sequences used in Example 1, where the exceptions or alternatives to the sequences shown are noted in the Materials and Methods section of Example 1 below. In each system, there are two fundamental DX units, designated A and B, and, additionally an alternative form B' that contains two hairpin-terminated bulged 3-arm junctions similar to the DX+J motif (Li et al, 1996). Based on studies of bulged 3-arm junctions (Ouporov et al, 1995), it is expected that in each unit, one hairpin will point up and out of the plane of the DX crystal, while the other hairpin will point down and into the plane, without significantly affecting the rigidity of the molecule (Li et al, 1996). The B' units replace the B units to serve as contrast agents for AFM imaging, because their increased height can be measured directly. Related sequences were used for the four-unit lattice ABCD' and for studies involving gold labelling or alternative placements of the hairpins. FIGS. 9A–9E show the DX units, A, B(B^ or B°), C, and D*, along with their sequences used as components in the four component arrays tested in Example 2.

Instead of hairpin-terminated bulged 3-arm junctions, one or more antiparallel nucleic acid multi-crossover components in a two-dimensional lattice can have at least one bulged 3-arm junction with a third helical arm pointing out of the plane of the two-dimensional lattice and terminating at a sticky/cohesive end. By providing corresponding complementary sticky/cohesive ends on a third helical arm pointing out of the plane of another two-dimensional lattice, two dimensional lattices can be stacked one on top of the other by covalent attachment at cohesive ends. In this manner, the two-dimensional lattices can be extended into three-dimensional lattices. Furthermore, the third helical arms of two bulged 3-arm junctions disposed parallel to each other on an antiparallel nucleic acid multi-crossover molecule can be designed to form crossover sites, thereby adding rigidity when connected to corresponding third helical arms of another antiparallel nucleic acid multi-crossover molecule in a parallel plane to extend lattices into three dimensions.

It should be appreciated that the term "nucleic acid" refers to both DNA and RNA and hybrids of the two. The structure need not resemble anything which can theoretically be made from nature.

A particular oligonucleotide or polynucleotide strand may employ bases other than the standard five, adenine, cytosine, guanine, thymine and uracil. Derivatized (e.g., methylated) and other unusual bases such as iso-guanine, iso-cytosine, amino-adenine, K, X, π, (Piccirilli et al, 1990), inosine and other derivatives of purine and pyrimidine may be used as well as any differently configured nucleotides, such as pseudouridine, pseudocytidine, or pseudoisocytidine. A preferable feature in the selection of the bases is that they be capable of interacting with a base opposing them to form a specifically paired attraction. In natural DNA and RNA, hydrogen bonding forms this interaction. However, opposite ion charges, hydrophobic interactions and van der Waals forces may also be acceptable forms of interaction. These interactions expand the choices over naturally occurring bases to give a wider assortment of physical properties.

Within a particular strand, the heterocyclic base may be entirely missing from the sugar moiety. This may be particularly desirable where the strands bend, form a junction, or where one desires fewer forces holding the strands together.

A particular strand need not have a single contiguous ribose-phosphate or deoxyribose-phosphate backbone. One may employ a simple inorganic or organic moiety or polymeric spacer between segments of polynucleotide. Spacers such as polyethylene, polyvinyl polymers, polypropylene, polyethylene glycol, polystyrene, polypeptides (enzymes, antibodies, etc.) peptide nucleic acids (PNA), polysaccharides (starches, cellulose, etc.) silicones, silanes and copolymers, etch, may be employed. An example of such a hybrid structure is dodecadiol having phosphoramidite at one end. This structure has been inserted covalently instead of four T nucleotides to form a hairpin loop in a fashion similar to the nucleotides it replaces (Doktycz, 1991). The term "oligonucleotide", "polynucleotide" and "nucleic acid" are intended to cover all of these structures.

In nature and the field of molecular biology, double stranded DNA generally occurs in the B form. However, for the purposes of this invention it may be desirable for DNA or other double stranded polynucleotide to exist in the A, C, D or Z form. Various bases, derivations and modifications may be used to stabilize the structure in the A, C, D or Z form as well.

The two-dimensional and three-dimensional periodic lattices according to the present invention can be self-assembled from individual nucleic acid strands of the antiparallel multi-crossover molecules. The present inventors have discovered that self-assembly can occur from an initial mixture, where all strands are present and mixed together, or in a stepwise fashion where the individual antiparallel multi-crossover molecule components of a multi-component lattice are first self-assembled separately and then mixed together to form multi-component lattices by joining individual components by complementary cohesive ends. In the self-annealing process, single-stranded polynucleotides are mixed together and heated at a temperature above the melting or denaturation temperature of the complementary strands, e.g., 90° C., to eliminate any initial secondary structure present in the mixture, and then cooled slowly or in a stepwise manner to allow the strands to anneal based on sequence complementarity. After annealing, and despite the presence of nicks in the strands, such as staggered nicks at cohesive ends, two-dimensional and three-dimensional lattices are produced. Enzymatic or chemical ligation to seal the nicks further stabilizes the lattice formed.

The periodic repeating units illustrated in the Figures are composed of either two or four individual DX units. However, the number of component tiles in the repeat unit is not limited to such small numbers, and complex patterns can be assembled into periodic arrays. These patterns could be either direct targets in nanofabrication or aids to the construction of such targets. Because oligonucleotide synthesis can readily incorporate modified bases at arbitrary positions, it should be possible to control the structure within the periodic block by decoration with chemical groups, catalysts, enzymes and other proteins (Niemeyer et al (1994), metallic nanoclusters (Alivisatos et al, 1996; Mirkin et al, 1996), conducting silver clusters (Braun et al, 1998), DNA enzymes (Breaker et al, 1994) or other DNA nanostructures, such as polyhedra (Chen et al, 1991; Zhang et al, 1994a). WO 95/34890, the content of which is herein incorporated by reference, discloses multiple chromophoric memory units for photo-write operation. The self-assembling lattices according to the present invention can provide the backbone for such photo-write operation.

Moreover, the third helical arm extending out of the plane in a bulged-three arm junction of an antiparallel nucleic acid multi-crossover molecule can be used to attach other molecules of interest, such as chemically or biologically active molecules, binding molecules, etc., and can be distorted as needed to accommodate the molecule of interest. For instance, the third helical arm can emanate from the bulged junction at virtually any angle relative to the parallel helical domains of an antiparallel multi-crossover molecule.

When extending the two-dimensional lattices into three dimensions, the designed crystals could potentially serve as scaffolds for the crystallization of macromolecules (Seeman, 1982), as photonic materials with novel properties (Joannopolous et al, 1995), as designable zeolite-like materials for use as catalysts or as molecular sieves (Ribeiro et al, 1996), and as scaffolds for the assembly of molecular electronic components (Robinson et al, 1987) or biochips (Haddon et al, 1985). The two-or three-dimensional lattices according to the present invention may also be used to create a mesh or screen-like material which can serve as a filter of very precise porosity.

Having now described the invention, the same will be more readily understood through reference to the following example which is provided by way of illustration and is not intended to be limiting of the present invention.

EXAMPLE 1

Both the DAO-E and DAE-O systems were investigated in parallel to illustrate that the same principles of self-assembly govern both systems. Therefore, except where noted, the discussion in this example will apply to both systems.

Materials and Methods

The following general procedures were used in the this example:

DNA Sequences and Synthesis

The DNA sequences for the individual strands of each unit type, e.g., A, B, B', etc., in the lattices formed in FIGS. 7A–7F and FIGS. 8A–8F are presented below in Table 1 based on the strand numbering according to FIGS. 5C–5H.

TABLE 1

| Lattice | Unit Type | Strand 1 SEQ ID | Strand 2 SEQ ID | Strand 3 SEQ ID | Strand 4 SEQ ID | Strand 5 SEQ ID |
|---|---|---|---|---|---|---|
| DAO-E AB (FIG. 7A) | A | NO:1 | NO:2 | NO:3 | NO:4 | — |
|  | B | NO:22 | NO:13 | NO:10 | NO:11 | — |
| DAO-E AB' (FIGS. 7B–7C) | A | NO:1 | NO:2 | NO:3 | NO:4 | — |
|  | B' | NO:21 | NO:13 | NO:19 | NO:20 | — |
| DAO-E AB' (FIGS. 8A–8C) | A | NO:1 | NO:21 | NO:3 | NO:4 | — |
|  | B' | NO:22 | NO:13 | NO:19 | NO:20 | — |
| DAO-E AB (FIGS. 6 and 7D) | A | NO:26 | NO:6 | NO:25 | NO:24 | NO:9 |
|  | B | NO:14 | nucleotides 1–21 of SEQ ID NO:15 | NO:28 | NO:17 | NO:18 |
| DAO-E AB' (FIG. 7E) | A | NO:5 | NO:6 | NO:7 | NO:8 | NO:9 |
|  | B' | NO:30 | NO:15 | NO:29 | NO:17 | NO:27 |
| DAO-E AB' (FIG. 7F) | A | NO:5 | NO:6 | NO:7 | NO:8 | NO:9 |
|  | B' | NO:23 | NO:15 | NO:16 | NO:17 | NO:27 |
| DAE-O ABCD' (FIGS. 8E–8F) | A | NO:34 | NO:31 | NO:33 | NO:32 | NO:35 |
|  | B | NO:39 | NO:36 | NO:38 | NO:37 | NO:40 |
|  | C | NO:44 | NO:41 | NO:43 | NO:42 | NO:45 |
|  | D' | NO:49 | NO:46 | NO:48 | NO:47 | NO:50 |

All oligonucleotides were synthesized by standard methods, PAGE purified, and quantitated by UV absorption at 260 nm in $H_2O$.

Annealing of Oligonucleotides

The strands of each DX unit were mixed stoichiometrically and dissolved to concentrations of 0.2 to 2 μM in TAE/$Mg^{++}$ buffer (40 mM Tris-HCl (pH 8.0), 1 mM EDTA, 3 mM Na$^+$, 12.5 mM Mg$^{++}$) or in a HEPES buffer (10 mM HEPES, 60 mM MgCl$_2$, 1 mM EDTA). The solutions were annealed from 90° C. to room temperature over the course of several hours in a Perkin-Elmer PCR machine (to prevent concentration by evaporation) or were annealed from 100° C. to room temperature during 40 hours in a 2 liter water bath insulated in a styrofoam box. To produce lattices, equal amounts of each DX were mixed and annealed from 50° C. to 20° C. over the course of up to 36 hours. In some cases (FIGS. 11A–11C) all strands were mixed together from the very beginning.

Gel Electrophoresis Studies

For gel-based studies, T4 polynucleotide kinase (Amersham) was used to phosphorylate strands with $^{32}$P; these strands were then PAGE purified and mixed with an excess of unlabeled strands. Non-denaturing 4%, 5%, or 8% PAGE (19:1 acrylamide:bisacrylamide) in TAE/Mg$^{++}$ was performed at 4° C. or at room temperature. For denaturing experiments, after annealing in T4 DNA ligase buffer (Amersham) (66 mM Tris-HCl pH 7.6), 6.6 mM MgCl$_2$, 10 mM DTT, 66 $\mu$M ATP), 1 $\mu$l=10 units T4 DNA ligase (Amersham) was added to 10 $\mu$l DNA solution and incubated for up to 24 hours at 16° C. or at room temperature. For exonuclease reactions, 50 units of exonuclease III (Amersham) and 5 units of exonuclease I (Amersham) were added after ligation, and incubated an additional 3.5 hours at 37° C. The solution was added to an excess of denaturing dye buffer (0.1% xylene cyanol FF tracing dye in 90% formamide with 1 mM EDTA, 10 mM NaOH) and heated to 90° C. prior to loading. Denaturing gels contained 4% acrylamide (90:1 acrylamide:bisacrylamide) and 8.3 M urea in TBE (89 mM Tris:HCl (pH 8.0), 89 mM boric acid, 2 mM EDTA). Gels were analyzed by phosphorimager.

Labelling with Biotin-Streptavidin-Nanogold

The central strand of DAE-O B was synthesized containing a 5' biotin group. Lattices were formed by annealing as described above. After annealing, a stoichiometric amount of streptavidin-nanogold (1.4 nm, Nanoprobe, Inc., Stonybrook, N.Y.) in a buffer provided by the supplier (20 mM phosphate, 150 mM NaCl (pH 7.4), 0.1% BSA, 0.05% NaN$_3$) was added, so that the molar ratio of biotin to streptavidin was 1:1. The solution was left at room temperature for 1 hour, and then imaged by AFM as described below.

Preparation of AFM Sample 2 to 10 $\mu$l were spotted on freshly cleaved mica (Ted Pella, Inc.) and left to adsorb to the surface for 2 minutes. To remove buffer salts, 5 to 10 drops of doubly-distilled or nanopure H$_2$O were placed on the mica, the drop was shaken off and the sample was dried with compressed air. Imaging was performed under isopropanol in a fluid cell on a NanoScope II using the D or E scanner or commercial 200 $\mu$m cantilevers with Si$_3$N$_4$ tips (Digital Instruments). The feedback setpoint was adjusted frequently to minimize contact force to approximately 1 to 5 nN. Images were processed with a first- or third-order "flatten filter," which independently subtracts a first- or third-order polynomial fit from each scanline to remove tip artifacts; however, this technique can introduce false "shadows."

Results

Characterization of DX Units and Lattices by Gel Electrophoresis

A prerequisite for lattice self-assembly is the formation of the DX units from their component strands. A thorough investigation of this issue was done for the original studies of DX (Fu, 1993); and the finding that the new designs also behave well constitutes further validation of the antiparallel DX motif. Because the sticky ends of A units have affinity only for sticky ends of B units, and not for themselves, neither A nor B alone in solution can assemble into a lattice. Thus the formation of isolated DX units can be monitored easily by non-denaturing gel electrophoresis, as described previously (Fu, 1993), and greater than 95% of the material is seen in the expected band.

Solutions containing A and B units can be mixed and annealed to form AB lattices. Enzymatic ligation of these lattices with T4 DNA ligase should produce long covalent DNA strands. The nicks, where strands from adjacent DX units abut, are all on the upper or lower surface of the lattice, where they are accessible to the enzyme. The long strands can serve as reporters of successful lattice formation. In the DAO-E design there are four vertical reporter strands, whereas in the DAE-O design there are two horizontal and two vertical reporter strands. All four reporter strands extend for more than 30 repeats when visualized by denaturing polyacrylamide gel electrophoresis (PAGE) (FIG. 10; data for DAO-E not shown). Longer strands co-migrate on this gel, so the full extent of polymerization cannot be determined. These results suggest that the lattice is a good substrate for T4 DNA ligase, and that the lattices can form with more than 30x30 units. However, unintended associations or side reactions could lead to similar distributions of strand lengths after ligation and direct physical observation, such as by atomic force microscopy imaging, is necessary to confirm lattice assembly.

AFM Imaging of AB Lattices

Atomic force microscopy (Binnig et al, 1986) was used to unequivocally demonstrate the formation of 2-D lattices. A and B units were annealed separately, then combined and annealed together to form AB lattices. The resulting solution was deposited for adsorption on an atomically flat mica surface, and then imaged under isopropanol by contact mode AFM (Hansma et al (1992). The solution was not treated with DNA ligase, and thus the lattices were held together only by non-covalent interactions (e.g. hydrogen bonds and base stacking). This protocol ensures that the solution contains no protein contaminants. Negative controls of buffer alone and of A or B alone showed no aggregates larger than 20 nm (data not shown). In separate experiments, A and B DAO units were modified by the removal of two sticky ends from each unit; when the modified A and B units were annealed together, only linear and branched structures with apparent widths typically less than 10 nm were observed (data not shown), providing additional negative controls. However, the unmodified AB samples contained 2-D sheets many microns long, often more than 200 nm wide (FIGS. 11A, 11D). The apparent height of the sheets is 1.4+0.5 nm, suggesting a monolayer of DNA. The sheets often seem ripped and appeared to have a grain, in that rips have a preferred direction consistent with the design (FIGS. 2C and 2D). In the DAO-E lattice, a vertical rip requires breaking six sticky-end bonds per 12 nm torn, whereas a horizontal rip requires breaking only one sticky-end bond per 13 nm torn. A possible vertical column, perpendicular to the rips, is indicated in FIG. 11A (arrows). Although in this image the columns are barely perceptible, Fourier analysis showed a peak at 13+1 nm, suggesting that the observed columns were 1 DX wide. Periodic topographic features would not be expected in the ideal AB lattice; however a vertically stretched lattice may have gaps between the DX units that could produce the periodic features seen here. Because crystals were found in AFM samples taken from both the top and the bottom of the solution, the crystals were believed to be formed in solution and not due to interaction with a surface.

Surface Topography in AB' and ABCD' Lattices

The self-assembling AB lattice can serve as scaffolding for other molecular structures. AB' unit is a B unit decorated with two DNA hairpin sequences inserted into its component strands (FIGS. 5G and 5H). So decorated, the vertical columns of the lattice become strikingly apparent as stripes in AFM images (FIGS. 11B, 11C, 11E, 11F), further confirming the proper self-assembly of the 2-D lattice. The spacing of the decorated columns is 25±2 nm for the DAO-E lattice and 33±3 nm for the DAE-O lattice, indicating that every other column is decorated, in accord with the design. Slow annealing at 20° C. and gentle handling of the DAO-E sample during deposition and washing has produced single crystals measuring up to 2×8 μm (FIGS. 12A–12C). Close examination showed that the stripes are continuous across the crystal, and thus it appears to be a single domain containing over 500,000 DX units.

Instead of DNA hairpins, other chemical groups can be used to label the DX molecules. Previous groups have used biotin-streptavidin-gold to label linear DNA for imaging by AFM (Shaiu et al, 1993a; Shaiu et al, 1993b). 1.4 nm nanogold-streptavidin conjugates were used to label DAE molecules. For these experiments, the central strand of B contains a 5' biotin group. After assembly of AB lattices, the solution containing DNA lattices was incubated with streptavidin-nanogold conjugates and then imaged by AFM (FIG. 12D). That the nanogold particles remain conjugated to the streptavidin molecules was not confirmed, and the surface topography may be due to streptavidin molecules alone.

DAO and DAE systems incorporating only one of the two hairpins in B', DAO systems in which the 3-arm junctions are relocated by two nucleotides toward the center of the molecule, and DAE systems in which the arms are one nucleotide longer or shorter were tested. All systems produced results similar to those shown in FIGS. 11A–11D when imaged by AFM (data not shown). The lattice assembly appears to be robust to variations in the local DX structure and is not sensitive to small variations in the annealing protocol. The results reported here were obtained in two separate laboratories of the present inventors using different buffers, annealing conditions, and AFM instruments.

Choice of sticky ends predictably determines the associations between DX units. Therefore, it is straightforward to modify the AB system into a four DX system with twice the period (FIG. 2B). This requires the use of twice as many unique sticky end sequences to control the unique association of DX units A, B, C, and D. Such a system was created in the DAE-O topology, where a single unit, D', was decorated with two hairpins. Crystals in this system showed stripes spaced every 66+5 nm, confirming that every fourth vertical column was decorated (FIGS. 12E and 12F).

In all images of AB, AB', and ABCD' systems, many DNA structures were observed in addition to the isolated 2-D crystals discussed above. In many images, the 2-D crystals appear to overlap, leading to discrete steps in thickness (FIGS. 11C, 12A, 12D). The arrangement of crystals on the mica-solitary, overlapping, piled up like driftwood, ripped to shreds-depends sensitively upon DNA concentration and upon the sample preparation procedure, especially the wash step. Prominently, the background of every image contains small objects, which are assumed to be associations of small numbers of DX units. Also, long, thin "rods" appear in some preparations (FIGS. 11F and 12D). These structures have not yet been characterized.

EXAMPLE 2

As shown in Example 1, hydrogen-bonded two-dimensional crystals can be formed from DX molecules and these arrays can be observed by atomic force microscopy (AFM). The sticky ends that hold the arrays together can be varied, so as to include diverse periodic arrangements of molecules in the crystal. The inclusion of extra DNA hairpins designed to protrude from the plane of the crystal provides a topographic label that is detected readily in AFM images. By using these labels, stripes at predicted spacings on the surface of the crystal can be produced.

Ordered DX assemblies can be regarded as a basic substrate on which chemical operations can produce both useful modifications and varied patterns. The experiments presented below demonstrate that these patterns can be modified by both enzymatic and nonenzymatic procedures. For example, the addition of protruding hairpins to specific sites on a crystal or their removal could be used to alter the properties, the pattern, or the information content of the substrate. It is demonstrated here that features can be added to a 2D DNA crystal by ligating or by hydrogen bonding hairpins to it, and conversely, hairpins with a restriction enzyme recognition site can be removed by the use of restriction enzymes. Annealing a hairpin to a crystalline array by hydrogen bonding can occur in solution or after deposition on a mica surface. Thus, from a small set of starting DX crystal components, it is possible to produce a diversity of ordered DNA arrays, each displaying different surface features.

Materials and Methods

The following procedures were used in this example:

Synthesis and Purification of DNA

All DNA molecules in this study have been synthesized on an Applied Biosystems 380B automatic DNA synthesizer, removed from the support, and deprotected, using routine phosphoramidite procedures (Caruthers, 1985). DNA strands have been purified by electrophoresis; bands are cut out of 12–20% denaturing gels and eluted in a solution containing 500 mM ammonium acetate, 10 mM magnesium acetate, and 1 mM EDTA.

Formation of Hydrogen-Bonded Arrays

Complexes are formed by mixing a stoichiometric quantity of each stand, as estimated by $OD_{260}$. Exact stoichiometry is determined, if necessary, by titrating pairs of strands designed to hydrogen bond together and visualizing them by nondenaturing gel electrophoresis; absence of monomer is taken to indicate the endpoint. All 20 strands are mixed either in 10 mM HEPES (pH 7.8), 6 mM $MgCl_2$, and 1 mM EDTA (for restriction) or 20 mM Tris (pH 7.6) and 10 mM $MgCl_2$ (for restriction or ligation). The final concentration of DNA is 0.4 μM, and the final volume is 50 μL. The tube containing the DNA solution is put in about 2 L of boiled water and placed in a Styrofoam box for at least 40 h to facilitate hybridization.

Enzymatic Reactions

A. Phosphorylation

An individual strand of DNA (100 pmol) is dissolved in 10 μL of a solution containing 50 mM Tris-HCl (pH 7.6), 10 mM $MgCl_2$, 10 mM 2-mercaptoethanol, and 1 mM ATP and incubated with 3 units of polynucleotide kinase (Amersham) for 120 min at 37° C. The reaction is stopped by heating the solution to 90° C. for 10 min, followed by gel purification.

B. Restriction of Arrays

Five units of PvuII (New England Biolabs, Beverly, Mass.) is added to a 20 μL aliquot of a solution containing arrays, which is ten incubated for 1.5 h at 37° C. The array is then imaged directly.

Ligation to Arrays

The two hairpin strands are added to a 12.5 μL aliquot of the annealed lattice. The molar ratio of sticky ends on the lattice to each hairpin is 1:2, the final ligation volume is 25 µL, and the final DNA concentration of array components is 0.2 µM. The ligation solution contains 20 mM Tris (pH 7.6), 10 mM MgCl$_2$, 0.4 mM ATP, and 1 mM DTT. This ligation solution is incubated in about 2 L of water (37° C.) and cooled slowly to about 10° C. At that point, 5 units of T4 DNA ligase (Amersham) are added to the solution and incubated overnight at 16° C. After ligation, the product is dialyzed against 2 L of a solution containing 10 mM HEPES (pH 7.8), 6 mM MgCl$_2$, and 1 mM EDTA in a microdialysis system whose reservoir is circulated by a pump.

Hydrogen Bonding of Hairpins

Hairpins are incubated with the array in the same conditions used for ligation, but no dialysis is performed.

AFM Imaging

A 3–5 µL aliquot of a solution containing arrays is deposited on a freshly cleaved mica surface for 1.5 min. It is then washed with double-distilled water and dried with compressed air. Samples were imaged under 2-propanol in a fluid cell on a NanoScope II and commercial 100 or 200 µm oxide-sharpened silicon nitride oriented twin tips (Digital Instruments).

Results

Molecules Used in Enzymatic Modification of 2D DNA Crystals

The DX and DX+2J molecules used in the enzymatic modification experiments are shown in FIGS. 9A–9E. The sequences of the molecules have been designed using the program SEQUIN (Seeman, 1990) to minimize their sequence symmetry. The molecules labeled A, C, D* in FIGS. 9A, 9D, and 9E have been used in both of the enzymatic DNA array modification studies reported here. Molecules A and C are conventional DX molecules, a DNA motif that has been characterized extensively by gel electrophoresis and chemical probes. (Fu et al., 1993; Li et al., 1996; Fu et al., 1994; Zhang et al., 1994; and Li et al., 1997). The molecule labeled D* is a DX+2J motif, similar to one used in Example 1. Bulged three-arm branched junctions are used to produce the protruding hairpins, rather than conventional branched junctions. Bulged junctions are used because the presence of the bulge supplies the leeway necessary for the DX helical domain to maintain its stacking without distortion (Liu et al., 1995).

The molecule labeled B^ is a DX+2J molecule that has been used in the experiments involving modification of the 2D array by restriction. Each of its two bulged junction hairpins contains 12 nucleotide pairs and a loop consisting of dT$_4$. In addition, each contains a 5'CAGCTG-3' sequence; this is the recognition site for cleavage by PvuII restriction endonuclease. This enzyme has been chosen deliberately because the products of its digestion are blunt-ended fragments; blunt-ended fragments do not require special treatment (Qi et al., 1996) to be removed after cleavage. The site has been located within the bulged hairpin so that only five nucleotide pairs (and the bulge) remain after scission.

It is important to realize that D* does not contain the PvuII recognition site.

The molecule labeled B° is a DX+2J molecule that has been used in experiments involving ligation of hairpins to the array. Both the molecule B° and the two hairpins to be ligated to it are shown in FIG. 9C. Its size and sticky ends within the plane of the array are the same as those of B^. The nonplanar part of B° is similar to the product of digesting B^ with PvuII because its bulged arm contains five nucleotide pairs. However, it also contains two asymmetric (non-self-complementary) sticky ends, 5'-GACACC-3' and 5'CGAAGC-3', that are used for the ligation of hairpin loops. Following ligation, the intact product contains 16 nucleotide pairs, in addition to the dT$_4$ hairpin loop. The molecules used for hydrogen-bonded addition of hydrogen bonding are similar to B° and its hairpins, except that the sticky ends are twice as long (see below).

Modification of DNA Arrays by Restriction

FIGS. 13A and 13B illustrate the modifications performed on the arrays in a schematic fashion. The four components of the array to be restricted, molecules A, B^, C, and D*, are shown in an enlarged representation at the top of FIG. 13A. Each molecules is drawn as a pair of rectangles connected by two lines. The molecules are shaded uniquely, to clarify the way in which they form rows within the assembled crystal. The sticky ends of each molecule are represented as geometrical shapes at the left and right ends of the rectangles. Complementarity is indicated by complementary shapes on the ends of adjacent molecules; for example, the lower right side of A consists of a male V-shape, and the upper left side of B^ is a female V-shape. Both B° and D* are DX+2J molecules, and this fact is denoted by shaded circles at the centers of the molecules. The differences between the hairpins of B^ and D* are indicated by differences in the shading of these circles. The aim of the experiment is to change the pattern by digestion of the array by PvuII, so that the hairpin of B^ is removed, leaving a remnant of just five nucleotide pairs; this remnant is represented by an unfilled circle in the lower half of FIG. 13A.

The primary means of characterization is AFM observation of 2D crystalline arrays. FIG. 14A is an AFM image of the array built from A, B^, C and D. Stripes with a spacing of roughly 32 nm are the most prominent features of this array. This is the spacing expected for an unmodified array and is similar to the spacing observed previously for an array containing only two components, a conventional DX molecule, A, and a DX+2J molecule, B* from Example 1. FIG. 14B is an AFM image of an A-B^-C-D* array following digestion by PvuII. In this case, the most prominent feature of the array is a series of stripes separated by about 64 nm. The array is similar to one observed previously that contained four components, A, B, C, and D*, where A, B, and C are conventional DX molecules and D* is a DX+2J molecule. In addition to the major 64 nm stripes, a far less prominent striped feature is visible halfway between these stripes. This stripe is likely to represent the residual bulged arm containing five nucleotide pairs (see below). The possibility that some intact hairpins remain cannot be excluded. This image also contains a certain amount of high (white) debris resulting from the contact of the array with the restriction enzyme extract.

The stability of the A-B^-C-D* arrays under the 37° C. restriction conditions was checked by AFM; this control experiment has been performed to be sure that intact arrays, and not their components, are the substrates of the restriction enzyme. The arrays have been incubated for 1.5 h at 37° C. and then placed them in the AFM at room temperature. The arrays appear to be stable under these conditions; they are not known to assemble on the support, so rapid formation is not being observed. The proportion of material in arrays after incubation also appears to be normal (data not shown).

Modification of DNA Arrays by Ligation

FIG. 13B illustrates the ligation of sticky-ended DNA hairpins to the arrays, the complementary experiment to restriction. Three of the components, A, C, and D*, are exactly the same as in the previous experiment, illustrated in FIG. 13A. The difference here is that B^ has been replaced by B°, a different DX+2J molecule. Rather than a pair of hairpins in its bulged arms, it contains a pair of short double helices (five nucleotide pairs) terminating in six-nucleotide sticky ends. The experiment here is to ligate hairpins to those sticky ends; only the sticky ends associated with ligation contain phosphate groups. As illustrated in FIG. 13B, the ligation is expected to produce an array resembling the starting material in FIG. 13A, although the hairpins are slightly longer.

FIG. 1SA shows an AFM image of the starting crystalline array for this experiment. The image is characterized by alternating rows of prominent stripes and secondary stripes. FIG. 15A resembles FIG. 14B closely, suggesting that the prominent stripes result from the D* molecules and that the secondary stripes are the short arms on the B° molecules. From this observation, it is possible to infer that the less prominent stripes of FIG. 14B are indeed the residual hairpins left after restriction of the A-B^-C-D* array. FIG. 15A indicates that the separation of the prominent stripes is about 64 nm. FIG. 15B is an AFM image of the product of the ligation reaction. It is clear that the differences between the stripes have disappeared. Both images of the product contain stripes of equally strong prominence, separated by about 32 nm; these product images are consistent with successful ligation of the hairpins to the array.

Hydrogen Bonding of Hairpins to DNA Arrays

It was also found that it is also possible to attach hairpins noncovalently, annealed by means of hydrogen bonding. The six-nucleotide sticky ends of the B° molecules are not long enough to stabilize the noncovalent attachment of hairpins to the arrays. Nevertheless, this means of attachment can be used, if one lengthens the sticky ends to 12 nucleotides (5'-CGATTCCGAAGC-3' (SEQ ID NO:80) and 5'-GCTCCAGACACC-3' (SEQ ID NO:81) on the DX+2J molecules and their complements on the hairpins), so that the hairpins ultimately contain 22 nucleotide pairs. A variation on the D* hairpin containing 22 nucleotide pairs is also used. FIG. 16A is an AFM image of the array before annealing the additional hairpins; it is very similar to FIG. 15A, showing a 64 nm spacing of prominent stripes, alternating with weaker stripes halfway between them. FIG. 16B shows a array after the hairpins have annealed, where the 32 nm spacing is prominent. This arrangement is similar to that seen in the ligation experiment shown in FIG. 15B. The extent of modification is also similar to that of the ligation experiment. In addition, the hairpins are able to be annealed to the exposed surface of the array when it is attached to the surface (data not shown).

Discussion

Modification of the Arrays

A pair of complementary modifications to hydrogen-bonded arrays of DNA tiles that alter the covalent structures of their components have been described and it has been shown that it is possible both to remove and to add hairpins that produce topographic features on the mesoscopic scale. The extent of restriction appears to be virtually complete, and only a few positions of ligation failure are detectable. Hairpins can also be added to the 2D DNA crystal by noncovalent attachment. It is important to point out that the enzymatic operations on arrays have been performed in solution; the enzymology deposited on the mica support. Nevertheless, the attachment of hairpins to long sticky ends by hydrogen bonding them after the array has been deposited has been successful.

Potential Applications of Array Modification 2D tilings of the plane in Example 1 demonstrated that, in principle, it is possible to construct virtually any periodic surface pattern, with a sufficient diversity of components. The work presented in this example suggests that the same components can lead to altered properties or multiple patterns, thereby lessening the expense of synthesis and increasing the flexibility of the design. Altered properties could be obtained by adding or removing hairpins that contain fluorescent labels or sites for protein decoration (Smith et al., 1997).

As an example of increased pattern diversity, the one-dimensional striped system described in this example can be expanded from two stripes to a larger number, each with a different restriction site, or containing a different sticky end. Each of these sites could be modified individually by restriction or by ligation. For simplicity, let us say there are four different rows that can contain a hairpin or not, in a system that could be called A-B*-C-D#-E-F^G-H*, where each of the nonalphabetic symbols represents a different hairpin or hairpin attachment site. Therefore, $2^4$ (=16) different patterns could be produced from eight starting components in about 128 running nanometers, using any of the systems described here. Similarly, 20 components with 10 variable features could produce $2^{10}$ (=1024) patterns. Clearly, some means of phasing the array would be necessary: For example, DX+2J molecules on the normally blank components might be used; a grouping such as A*B*C*DE*F* would contain the right features to establish both the origin and orientation of the starting point. Alternatively, a protein that bound to a particular hairpin (Smith et al., 1997) could also delimit the border. Without such phasing, the number of distinct patterns in the four-stripe system would decrease from 16 to 6. In general, the number of patterns phased by a border will be $2^p$ for p-hairpin patterns that are not otherwise distinct to the AFM, but unphased patterns are markedly fewer; the number of unphased patterns is the same as the number of different necklaces that be made with p beads of two colors (Constantine et al., 1987).

It is evident how to extend this system to two dimensions, but the aspect ratio of DX molecules, ca. 4×1, would lead to some extra effort. A p×q repeat unit assembled with 16 nm square tiles could be made with 4 pg tiles, assuming a feature every 32 nm. However, 16pq tiles would be necessary if 16×4 nm DX molecules were used in both directions.

It is clear that global treatment involving restriction or ligation will lead to a periodic array containing the same repetitive pattern. If one wished to store information in the array, some means would be needed to modify the array locally after deposition on a support. It is possible to manipulate molecules individually by means of scanning probe microscopic techniques (Jung et al., 1996). If one could restrict, ligate, bind, or dissociate locally, this system could be converted into a means of writing information very densely. The information could then be read by a scanning probe instrument, such as the AFM used in this work.

Having now fully described this invention, it will be appreciated that by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional method steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Adleman, L. M., "Molecular computation of solutions to combinatorial problems", Science 266:1021–1024 (1994).

Alivisatos et al, "Organization of 'nanocrystal molecules' using DNA", Nature 382:609–611 (1996).

Arnott et al J. Mol. Biol. 81:93–105 (1973).

Binnig et al, "Atomic force microscope", Phys. Rev. Lett. 56:930–933 (1986).

Braun et al, "DNA-templated assembly and electrode attachment of a conducting silver wire", Nature 391:775–778 (1998).

Breaker et al, "A DNA enzyme that cleaves RNA", Chem. Biol. 1:223–229 (1994).

Carter et al, "NAMOT2—a redesigned nucleic acid modelling tool: construction of non-canonical DNA structures", CABIOS 12:25–30 (1996).

Chen et al, "The synthesis from DNA of a molecule with the connectivity of a cube", Nature 350:631–633 (1991).

Cohen et al, "Construction of biologically functional bacterial plasmids „in vitrow", Proc. Nat. Acad. Sci. USA 70:3240–3244 (1973).

Constantine et al., Combinatorial Theory and Statistical Design, pp 233–236 (1987)

Doktycz, M. J., Ph.D. Thesis, University of Illinois, Chicago (1991).

Drexler, Proc. Nat. Acad. Sci. (USA) 78:5275–5278 (1981).

Feynman et al, Miniaturization 282–296 (1961).

Fu et al, "DNA double-crossover molecules" Biochem. 32:3211–3220 (1993).

Fu et al, Biochem. 33:3896–3905 (1994a).

Fu et al, J. Mol. Biol 236:91–105 (1994b).

Grunbaum et al, Tilings and Patterns (W. H. Freeman and Company, New York) 1986.

Haddon et al, "The molecular electronic device and the biochip computer: present status", Proc. Nat. Acad. Sci. USA 82:1874–1878 (1985).

Hansma et al, "Reproducible imaging and dissection of plasmid DNA under liquid with the atomic force microscope", Science 256:1180–1184 (1992).

Joannopolous et al, Photonic crystals: moulding the flow of light (Princeton University Press, Princeton, 1995).

Jung et al., Science, 271:181–184 (1996)

Leontis et al, Nucl. Acids Res. 19:759–766 (1991).

Li et al., Biochemistry, 36:4240–4247 (1997)

Li et al, "Antiparallel DNA double crossover molecules as components for nanoconstruction", J. Am. Chem. Soc. 118:6131–6140 (1996).

Liu et al, "Bulged 3 arm DNA branched junctions as components for nanoconstruction", Nanobiol. 3:177–188 (1994).

Ma et al, "Three-arm nucleic acid junctions are flexible", Nucl. Acids Res. 14:9745–9753 (1986).

Mirkin et al, "A DNA-based method for rationally assembling nanoparticles into macroscopic materials", Nature 382:607–609 (1996).

Niemeyer et al, "Oligonucleotide-directed self-assembly of proteins", Nucl. Acids Res. 22:5530–5539 (1994).

Ouporov et al, "Refinement of the solution structure of a branched DNA three-way junction", Biophys. J. 68:266–274 (1995).

Petrillo et al, "The ligation and flexibility of four-arm DNA junctions", Biopolymers 27:1337–1352 (1988).

Piccirilli et al, 343:33–37 (1990).

Qi et al, J. Am. Chem Soc., 118:6121–6130 (1996).

Qui et al, "A DNA decamer with a sticky end: The crystal structure of d-CGACGATCGT", J. Mol. Biol. 267:881–898 (1997).

Reif, J. "Local parallel biomolecular computing", in Proceedings of the 2$^{nd}$ DIMACS Meeting on DNA Based Computers, held at Princeton University, Jun. 10–12, 1996 (American Mathematical Society, Providence, R.I., in press).

Rhodes et al, "Helical periodicity of DNA determined by enzyme digestion", Nature 286:573–578 (1980).

Ribeiro et al, "Structure-activity relationships in zeolites", J. Mol. Cat. A: Chem. 96:245–270 (1996).

Robinson et al, "The design of a biochip: A self-assembling molecular-scale memory device", Prot. Eng. 1:295–300 (1987).

SantaLucia et al, "Improved nearest-neighbor parameters for predicting DNA duplex stability", Biochem. 35:3555–3562 (1996).

Schwacha et al, "Identification of double Holiday junctions as intermediates in meiotic recombination", Cell 83:783–791 (1995).

Seeman, N. C., "Nucleic acid junctions and lattices", J. Theor. Biol. 99:237–247 (1982).

Seeman, N. C., "„De novow design of sequences for nucleic acid structural engineering", J. Biomol. Str. & Dyns. 8:573–581 (1990).

Seeman, DNA & Cell Biol. 10:475–486 (1991a).

Seeman, Nanotechnol. 2:149–159 (1991b).

Shaiu et al, "Atomic force microscopy of oriented linear DNA molecules labelled with 5 nm gold spheres", Nucl. Acids Res. 21:99–103 (1993a).

Shaiu et al, "Visualization of circular DNA molecules labelled with colloidal gold spheres using atomic force microscopy", J. Vac. Sci. Tech. A. 11:820–823 (1993b).

Smith et al., Proc. Natl. Acad. Sci. U.S.A., 94:2162–2167 (1997)

Sun et al, Cell 64:1155–1161 (1991).

Sun et al, "Designing amino acid sequences to fold with good hydrophobic cores", Prot. Eng. 9:1205–1213 (1996).

Thaler et al, *Ann. Rev. Genet.* 22:169–197 (1988).
Vainshtein, B. K., *Modern Crystallography, Vol. 1: Fundamentals of Crystals* (Springer-Verlag, New York, 1994).
Wang et al, *Biochem.* 30:5667–5674.
Wang, H., "Dominoes and the AEA case of the decision problem", in *Proc. Symp. Math. Theory of Automata* (Polytechnic Press, New York, 1963), pp. 23–56.
Wang, J. C., "Helical repeat of DNA in solution", *Proc. Nat. Acad. Sci. USA* 76:200–203 (1979).
Whitesides et al, "Molecular self-assembly and nanochemistry: a chemical strategy for the synthesis of nanostructures", *Science* 254:1312–1319 (1991).
Winfree, E., "On the computational power of DNA annealing and ligation", in DNA Based Computers: Proceedings of a *DIMACS Workshop, Apr.* 4, 1995, *Princeton University* (Lipton et al, eds) (American Mathematical Society, Providence, R.I., 1996), pp. 199–221.
Winfree et al, "Universal computation via self-assembly of DNA: Some theory and experiments", in *Proceedings of the 2$^{nd}$ DIMACS Meeting on DNA Based Computers, held at Princeton University,* Jun. 10–12, 1996 (American Mathematical Society, Providence, R.I., in press).
Yue et al, "Inverse protein folding problem—designing polymer sequences", *Proc. Nat. Acad. Sci. USA* 89:4163–4167 (1992).
Zhang et al, "The construction of a DNA truncated octahedron", *J. Am. Chem. Soc.* 116:1661–1669 (1994a).
Zhang et al, *J. Mol. Biol.* 238:658–668 (1994b).

What is claimed is:

1. A periodic polynucleic acid structure, comprising a lattice of adjacent coplanar repeating units, each repeating unit comprising at least two antiparallel nucleic acid multi-crossover molecules, each of said at least two antiparallel nucleic acid multi-crossover molecules comprising two or more adjacent double helical domains, at least two of said two or more adjacent double helical domains having a first and second cohesive ends, each of said adjacent double helical domains having helix axes in parallel and being connected to adjacent double helical domains at two or more crossover sites, with each antiparallel nucleic acid multi-crossover molecules being connected to an adjacent antiparallel nucleic acid multi-crossover molecule by complementary cohesive ends, thereby forming an extended double helical domain between a first double helical domain of an antiparallel nucleic acid multi-crossover molecule and a second double helical domain of an adjacent antiparallel nucleic acid multi-crossover molecule, wherein a second double helical domain of said antiparallel nucleic acid multi-crossover molecule is not colinear and connectible with a first double helical domain of said adjacent antiparallel nucleic acid crossover molecule to form an extended double helical domain, and wherein each repeating unit is connected to an adjacent repeating unit in the same plane by complementary cohesive ends to form at least one extended double helical domain between adjacent repeating units in the same plane.

2. The periodic polynucleic acid structure according to claim 1, wherein said at least two antiparallel nucleic acid multi-crossover molecules of each repeating unit are coplanar.

3. The periodic polynucleic acid structure according to claim 1, wherein said at least two antiparallel nucleic acid multi-crossover molecules are antiparallel nucleic acid double crossover molecules.

4. The periodic polynucleic acid structure according to claim 1, wherein said at least two antiparallel nucleic acid multi-crossover molecules are antiparallel nucleic acid molecules having three double helical domains with parallel helix axes.

5. The periodic polynucleic acid structure according to claim 1, wherein said repeating units each comprises two different antiparallel nucleic acid multi-crossover molecules.

6. The periodic polynucleic acid structure according to claim 1, wherein said repeating units each comprises four different antiparallel nucleic acid multi-crossover molecules.

7. The periodic polynucleic acid structure according to claim 1, wherein said at least two antiparallel nucleic acid multi-crossover molecules are antiparallel nucleic acid multi-crossover having at least four double helical domains with parallel helix axes.

8. The periodic polynucleic acid structure according to claim 7, wherein one of said at least four double helical domains is a central double helical domain which is centrally located and surrounded by the remaining double helical domains of said at least four double helical domains.

9. The periodic polynucleic acid structure according to claim 7, wherein said at least four double helical domains are arranged with cylic symmetry.

10. The periodic polynucleic acid structure according to claim 7, wherein said at least two antiparallel nucleic acid multi-crossover molecules have four double helical domains with parallel helix axes.

11. The periodic polynucleic acid structure according to claim 7, wherein said at least two antiparallel nucleic acid multi-crossover molecules have six double helical domains with parallel helix axes.

12. The periodic polynucleic acid structure according to claim 1, wherein said lattice is two-dimensional.

13. The periodic polynucleic acid structure according to claim 1, wherein one or more of said at least two antiparallel nucleic acid multi-crossover molecules in each of said repeating units further comprises an additional helical domain whose helix axis is not parallel to the helix axes of said two or more adjacent helical domains, said additional helical domain having a first and second end, said first end of said additional helical domain forms a junction with one of said two or more adjacent helical domains.

14. The periodic polynucleic acid structure according to claim 1, wherein said lattice is extended into a third dimension.

15. The periodic polynucleic acid structure according to claim 14, wherein one or more of said at least two antiparallel nucleic acid multi-crossover molecules in each of said adjacent coplanar repeating units further comprises an additional helical domain whose helix axis is not parallel to the helix axes of said two or more adjacent helical domains, said additional helical domain having a first and second, wherein said first end of said additional helical domain forms a junction with one of said two or more adjacent helical domains and said second end of said additional helical domain is connected by a complementary cohesive end to a corresponding additional helical domain of an antiparallel nucleic acid multi-crossover molecule in a repeating unit disposed in a plane parallel to a plane formed of said at least two antiparallel nucleic acid multi-crossover molecules in each of said repeating units.

16. The periodic polynucleic acid structure according to claim 1, wherein said periodic polynucleic acid structure is self-assembling.

17. A method for producing a periodic polynucleic acid structure according to claim 1, comprising the steps of:

(a) synthesizing at least four single-stranded polynucleotides, each being self-complementary and/or complementary to another single-stranded polynucleotide, wherein the at least four single-stranded polynucleotides are capable of hybridizing together to form the at least two antiparallel nucleic acid multi-crossover molecules of each repeating unit;

(b) mixing the at least four single-stranded polynucleotides to form a mixture and heat denaturing the mixture;

(c) annealing the mixture of at least four single-stranded polynucleotides to form a lattice of repeating units of at least two adjacent antiparallel nucleic acid multi-crossover molecules; and (d) ligating complementary cohesive ends between adjacent antiparallel nucleic acid multi-crossover molecules to produce the periodic polynucleic acid structure.

* * * * *

SEQUENCE LISTING

<160> NUMBER OF SEQ ID NOS: 81

<210> SEQ ID NO: 1
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 1
tcactctacc gcaccagaat ggagat                                          26

<210> SEQ ID NO: 2
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 2
cataccgatc cgtggctact gtcttg                                          26

<210> SEQ ID NO: 3
<211> LENGTH: 48
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3
cattctggac gccataagat agcacctcga ctcatttgcc tgcggtag                  48

<210> SEQ ID NO: 4
<211> LENGTH: 48
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
cagtagcctg ctatcttatg gcgtggcaaa tgagtcgagg acggatcg                  48

<210> SEQ ID NO: 5
<211> LENGTH: 47
<212> TYPE: DNA

```
<213> ORGANISM: Artificial Sequence
<220> FEATURE:
<223> OTHER INFORMATION: Description of Artificial Sequence:
      Oligonucleotide

<400> SEQUENCE: 5
gatggcgaca tcctgccgct atgattacac agcctgagca ttgacac            47

<210> SEQ ID NO: 6
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6
gtagcgccgt tagtggatgt c                                        21

<210> SEQ ID NO: 7
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7
tgtagtatcg tggctgtgta atcatagcgg caccaactgg ca                 42

<210> SEQ ID NO: 8
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
gactgcgtgt caatgctcac cgatcaacca g                             31

<210> SEQ ID NO: 9
<211> LENGTH: 47
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
ctgacgctgg ttgatcggac gatactacat gccagttgga ctaacgg            47

<210> SEQ ID NO: 10
<211> LENGTH: 48
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
gctctacagg atctggtaag ttggtgtaac gtcggcttgt ccgttcgc            48

<210> SEQ ID NO: 11
<211> LENGTH: 48
<212> TYPE: DNA
<213> ORGANISM: Artificial Sequence
```

```
<220> FEATURE:
<223> OTHER INFORMATION: Description of Artificial Sequence:
      Oligonucleotide

<400> SEQUENCE: 11
gcggttgtcc aacttaccag atccacaagc cgacgttaca ggattgcc              48

<210> SEQ ID NO: 12
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12
gtatggcgaa cggtgtagag ccaaga                                      26

<210> SEQ ID NO: 13
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 13
agtgaggcaa tccacaaccg catctc                                      26

<210> SEQ ID NO: 14
<211> LENGTH: 47
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 14
cgctaccgtg catcatggac taaccagtga ccgcatcgga cagcagc               47

<210> SEQ ID NO: 15
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 15
cgtcaggctg ctgtggtcgt gc                                          22

<210> SEQ ID NO: 16
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 16
agtacaacgc caccgatgcg gtcactggtt agtggattgc gt                    42

<210> SEQ ID NO: 17
<211> LENGTH: 31
<212> TYPE: DNA
<213> ORGANISM: Artificial Sequence
<220> FEATURE:
```

-continued

<223> OTHER INFORMATION: Description of Artificial Sequence:
     Oligonucleotide

<400> SEQUENCE: 17
gccatccgtc gatacggcac catgatgcac g                                    31

<210> SEQ ID NO: 18
<211> LENGTH: 48
<212> TYPE: DNA
<213> ORGANISM: Artificial Sequence
<220> FEATURE:
<223> OTHER INFORMATION: Description of Artificial Sequence:
     Oligonucleotide

<400> SEQUENCE: 18
gcagtcgcac gacctggcgt tgtactacgc aatcctgccg tatcgacg                  48

<210> SEQ ID NO: 19
<211> LENGTH: 70
<212> TYPE: DNA
<213> ORGANISM: Artificial Sequence
<220> FEATURE:
<223> OTHER INFORMATION: Description of Artificial Sequence:
     Oligonucleotide

<400> SEQUENCE: 19
gctctacagg atctcgtagc agttttctgc tacgttggta agttggtgta acgtcggctt     60
gtccgttcgc                                                            70

<210> SEQ ID NO: 20
<211> LENGTH: 70
<212> TYPE: DNA
<213> ORGANISM: Artificial Sequence
<220> FEATURE:
<223> OTHER INFORMATION: Description of Artificial Sequence:
     Oligonucleotide

<400> SEQUENCE: 20
gcggttgtcc aactcctagc gattttttcgc taggtttacc agatccacaa gccgacgtta   60
caggattgcc                                                            70

<210> SEQ ID NO: 21
<211> LENGTH: 26
<212> TYPE: DNA
<213> ORGANISM: Artificial Sequence
<220> FEATURE:
<223> OTHER INFORMATION: Description of Artificial Sequence:
     Oligonucleotide

<400> SEQUENCE: 21
tcactcgatc cgtggctact ggagat                                          26

<210> SEQ ID NO: 22
<211> LENGTH: 26
<212> TYPE: DNA
<213> ORGANISM: Artificial Sequence
<220> FEATURE:
<223> OTHER INFORMATION: Description of Artificial Sequence:
     Oligonucleotide

<400> SEQUENCE: 22
agtgagcgaa cggtgtagag catctc                                          26

<210> SEQ ID NO: 23
<211> LENGTH: 69

```
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 23
cgctaccgtg catcatggac taaccagtgc tcgctgattt ttcagcgagt taccgcatcg    60
gacagcagc                                                            69

<210> SEQ ID NO: 24
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 24
cgactgcggt caatgctcac cgatcaacca g                                   31

<210> SEQ ID NO: 25
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 25
gcatgtagta tcgtggctgt gtaatcatag cggcaccaac tg                       42

<210> SEQ ID NO: 26
<211> LENGTH: 46
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 26
gatggcgaca tcctgccgct atgattacac agcctgagca ttgacc                   46

<210> SEQ ID NO: 27
<211> LENGTH: 70
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 27
gcagtcgcac gacctggcgt ctgttggctt ttgccaacag tttgtactac gcaatcctgc    60
cgtatcgacg                                                           70

<210> SEQ ID NO: 28
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 28
ggtcactggt tagtggattg cgtagtacaa cgccaccgat gc                       42
```

<210> SEQ ID NO: 29
<211> LENGTH: 64
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 29
actggttagt ggattgcgta ggcgagtagt tttctactcg ctttacaacg ccaccgatgc    60
ggtc                                                                 64

<210> SEQ ID NO: 30
<211> LENGTH: 47
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 30
cgctaccgtg catcatggac taaccagtga ccgcatcgga cagcagc                  47

<210> SEQ ID NO: 31
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 31
cacagcggta gcgtggacta g                                              21

<210> SEQ ID NO: 32
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 32
gactgccgac tggtgctcac cgtagttgct g                                   31

<210> SEQ ID NO: 33
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 33
gcagtacgtg tggcacaacg gcatgacata caccgatacg at                       42

<210> SEQ ID NO: 34
<211> LENGTH: 47
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 34
actatgctag tcctgtatgt catgccgttg tgcctgagca ccagtcg                  47

<210> SEQ ID NO: 35
<211> LENGTH: 47
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 35
ctgacgcagc aactacggac acgtactgca tcgtatcgga cgctacc          47

<210> SEQ ID NO: 36
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 36
caacgagcaa tcgtggctgc cg                                     22

<210> SEQ ID NO: 37
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 37
catagtcgta gtgtcatcac cagttgtatc g                           31

<210> SEQ ID NO: 38
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 38
acatacgcag tggatagcga ccaaccgtta caccgatgcg gt               42

<210> SEQ ID NO: 39
<211> LENGTH: 47
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 39
gctgtgcgat acaactggac tgcgtatgta ccgcatcgga cgattgc          47

<210> SEQ ID NO: 40
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 40
gtagcgccgt tagtggatgt c                                      21

<210> SEQ ID NO: 41
<211> LENGTH: 48
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 41
tgaactcggc agcctgtaac ggttggtcgc tatcctgatg acactacg            48

<210> SEQ ID NO: 42
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 42
agttcacggt caatgctcac cgatcaacca g                              31

<210> SEQ ID NO: 43
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 43
tgtagtatcg tggctgtgta atcatagcgg caccaactgg ca                  42

<210> SEQ ID NO: 44
<211> LENGTH: 47
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 44
gatggcgaca tcctgccgct atgattacac agcctgagca ttgacac             47

<210> SEQ ID NO: 45
<211> LENGTH: 47
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 45
tcgttgctgg ttgatcggac gatactacat gccagttgga ctaacgg             47

<210> SEQ ID NO: 46
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 46
cgtcaggctg ctgtggtcgt gc                                        22

<210> SEQ ID NO: 47
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 47
gccatccgtc gatacggcac catgatgcac g                                    31

<210> SEQ ID NO: 48
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 48
agtacaacgc caccgatgcg gtcactggtt agtggattgc gt                        42

<210> SEQ ID NO: 49
<211> LENGTH: 69
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 49
cgctaccgtg catcatggac taaccagtgc tcgctgattt ttcagcgagt taccgcatcg     60
gacagcagc                                                             69

<210> SEQ ID NO: 50
<211> LENGTH: 70
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 50
gcagtcgcac gacctggcgt ctgttggctt ttgccaacag tttgtactac gcaatcctgc     60
cgtatcgacg                                                            70

<210> SEQ ID NO: 51
<211> LENGTH: 47
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 51
actatgctag tcctgtatgt catgccgttg tgcctgagca ccagtcg                   47

<210> SEQ ID NO: 52
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 52

```
cacagcggta gcgtggacta g                                              21

<210> SEQ ID NO: 53
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 53
gcagtacgtg tggcacaacg gcatgacata caccgatacg at                       42

<210> SEQ ID NO: 54
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 54
gactgccgac tggtgctcac cgtagttgct gg                                  32

<210> SEQ ID NO: 55
<211> LENGTH: 48
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 55
ctgacgccag caactacgga cacgtactgc atcgtatcgg acgctacc                 48

<210> SEQ ID NO: 56
<211> LENGTH: 78
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 56
gcagtcgcac gacctggcgt tacagctggc atttttatgc cagctgtatt tgtactacgc   60
aatcctgccg tatcgacg                                                  78

<210> SEQ ID NO: 57
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 57
cgtcaggctg ctgtggtcgt gc                                             22

<210> SEQ ID NO: 58
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 58
```

```
gccatccgtc gatacggcac catgatgcac g                                        31

<210> SEQ ID NO: 59
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 59
agtacaacgc caccgatgcg gtcactggtt agtggattgc gt                            42

<210> SEQ ID NO: 60
<211> LENGTH: 77
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 60
cgctaccgtg catcatggac taaccagtgc tcagctgcct attttaggc agctgagtta          60 ccgcatcgga cagcagc                                                        77

<210> SEQ ID NO: 61
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 61
gcagtcgcac gacctggcgt ctcgt                                               25

<210> SEQ ID NO: 62
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 62
ggtgtcggct cttttgagcc                                                     20

<210> SEQ ID NO: 63
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 63
gacaccacga gtttgtacta cgcaatcctg ccgtatcgac g                             41

<210> SEQ ID NO: 64
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide
```

```
<400> SEQUENCE: 64
cgtcaggctg ctgtggtcgt gc                                           22

<210> SEQ ID NO: 65
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 65
agtacaacgc accgatgcgg tcactggtta gtggattgcg t                      41

<210> SEQ ID NO: 66
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 66
gccatccgtc gatacggcac catgatgcac g                                 31

<210> SEQ ID NO: 67
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 67
cgctaccgtg catcatggac taaccagtgg caac                              34

<210> SEQ ID NO: 68
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 68
gcttcgctga cttttgtcag                                              20

<210> SEQ ID NO: 69
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 69
cgaagcgttg cttaccgcat cggacagcag c                                 31

<210> SEQ ID NO: 70
<211> LENGTH: 47
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 70
```

```
gatggcgaca tcctgccgct atgattacac agcctgagca ttgacac              47

<210> SEQ ID NO: 71
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 71
gtagcgccgt tagtggatgt c                                          21

<210> SEQ ID NO: 72
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 72
tgtagtatcg tggctgtgta atcatagcgg caccaactgg ca                   42

<210> SEQ ID NO: 73
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 73
agttcagtgt caatgctcac cgattcaacc ag                              32

<210> SEQ ID NO: 74
<211> LENGTH: 48
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 74
tcgttgctgg ttgaatcgga cgatactaca tgccagttgg actaacgg             48

<210> SEQ ID NO: 75
<211> LENGTH: 82
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 75
tgaactcggc agcctgtaac gctggcaaca tgcttttag catgttgcca gcttggttgg  60
tcgctatcct gatgacacta cg                                         82

<210> SEQ ID NO: 76
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide
```

```
<210> SEQ ID NO: 77
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 77
accaaccgtt acaccgatgc ggtacatacg cagtggatag cg              42

<210> SEQ ID NO: 78
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 78
catagtcgta gtgtcatcac cagttgtatc g                          31

<210> SEQ ID NO: 79
<211> LENGTH: 81
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 79
gctgtgcgat acaactggac tgcgtatgtg tgacgtgctg acattttttgt cagcacgtca    60 cttaccgcat cggacgattg c                                     81

<210> SEQ ID NO: 80
<211> LENGTH: 12
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 80
cgattccgaa gc                                               12

<210> SEQ ID NO: 81
<211> LENGTH: 12
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 81
gctccagaca cc                                               12
```

<400> SEQUENCE: 76
caacgagcaa tcgtggctgc cg                                    22